US012297189B2

(12) United States Patent
Bolli et al.

(10) Patent No.: US 12,297,189 B2
(45) Date of Patent: *May 13, 2025

(54) CRYSTALLINE FORMS OF A 4-PYRIMIDINESULFAMIDE DERIVATIVE APROCITENTAN

(71) Applicant: IDORSIA PHARMACEUTICALS LTD, Allschwil (CH)

(72) Inventors: Martin Bolli, Allschwil (CH); Markus Von Raumer, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/319,402

(22) Filed: May 17, 2023

(65) Prior Publication Data

US 2023/0391757 A1    Dec. 7, 2023

Related U.S. Application Data

(63) Continuation of application No. 17/146,801, filed on Jan. 12, 2021, now Pat. No. 11,680,058, which is a continuation of application No. 16/489,194, filed as application No. PCT/EP2018/054627 on Feb. 26, 2018, now Pat. No. 10,919,881.

(30) Foreign Application Priority Data

Feb. 27, 2017   (WO) ................ PCT/EP2017/054489
May 12, 2017   (WO) ................ PCT/EP2017/061487

(51) Int. Cl.
C07D 403/12    (2006.01)
A61K 31/4035   (2006.01)
A61K 31/41     (2006.01)
A61K 31/4418   (2006.01)
A61K 31/506    (2006.01)
A61K 31/549    (2006.01)
A61P 9/12      (2006.01)
A61P 13/12     (2006.01)

(52) U.S. Cl.
CPC ........ *C07D 403/12* (2013.01); *A61K 31/4035* (2013.01); *A61K 31/41* (2013.01); *A61K 31/4418* (2013.01); *A61K 31/506* (2013.01); *A61K 31/549* (2013.01); *A61P 9/12* (2018.01); *A61P 13/12* (2018.01); *C07B 2200/13* (2013.01)

(58) Field of Classification Search
CPC ................................................. C07D 403/12
See application file for complete search history.

(56) References Cited

U.S. PATENT DOCUMENTS 7,094,781 B2   8/2006   Bolli et al.
7,285,549 B2   10/2007  Bolli et al.
8,101,599 B2   1/2012   Shetty et al.
8,324,232 B2   12/2012  Bolli et al.
8,475,839 B2   7/2013   Cao et al.
9,938,244 B2   4/2018   Abele et al.
10,919,881 B2 * 2/2021  Bolli ............... A61K 31/4035
11,174,247 B2  11/2021  Bellet et al.
11,234,980 B2  2/2022   Csonka et al.
11,680,058 B2 * 6/2023  Bolli ................. A61K 31/506
                                                            514/269
11,787,782 B2  10/2023  Bellet et al.
12,144,811 B2  11/2024  Bellet et al.
2012/0142716 A1  6/2012   Bolli et al.
2016/0368882 A1  12/2016  Abele et al.
2021/0169881 A1  6/2021   Bellet et al.
2022/0064149 A1  3/2022   Bellet et al.

FOREIGN PATENT DOCUMENTS

WO    WO 02/053557 A1     7/2002
WO    WO 03/097045 A1     11/2003
WO    WO 2007/098390 A2   8/2007
WO    WO 2007/146900 A2   12/2007
WO    WO 2009/024906 A1   2/2009
WO    WO 2009/026517 A2   2/2009
WO    WO 2015/121397 A1   8/2015
WO    WO 2016/073846 A1   5/2016
WO    WO 2017/185142 A1   11/2017
WO    WO 2018/153513 A1   8/2018
WO    WO 2019/106066 A1   6/2019

OTHER PUBLICATIONS

U.S. Appl. No. 12/673,413, filed Feb. 12, 2010, Bolli et al.
U.S. Appl. No. 15/118,046, filed Aug. 10, 2016, Abele et al.
U.S. Appl. No. 16/489,227, filed Aug. 27, 2019, Bellet et al.
"Characters Section in Monographs," European Pharmacopoeia 8.0, 5.11, 1 page.
Actelion Pharmaceuticals Ltd, "Actelion's Cardiovascular Pipeline Investor Webcast," Investor webcast, 52 pages (Nov. 7, 2016).
Actelion Pharmaceuticals Ltd, "Actelion provides an update on the progress towards launching Idorsia—Key results for pipeline assets to be developed by Idorsia," Media Release, pp. 1-7 (2017).
Abstracts, Clinical Pharmacology & Therapeutics, vol. 103, Supp S1, p. S87 (2018).
Atanur, S. et al., "The genome sequence of the spontaneously hypertensive rat: Analysis and functional significance," Genome Research, vol. 20, pp. 791-803 (2010).
Aversa, M. et al., "Comparative Safety and Tolerability of Endothelin Receptor Antagonists in Pulmonary Arterial Hypertension," Drug Saf, 17 pages (2015).

(Continued)

*Primary Examiner* — Paul V Ward
(74) *Attorney, Agent, or Firm* — Hoxie & Associates LLC

(57) ABSTRACT

The present invention concerns novel crystalline forms of {5-(4-bromo-phenyl)-6-[2-(5-bromo-pyrimidin-2-yloxy)-ethoxy]-pyrimidin-4-yl}-sulfamide, processes for the preparation thereof, pharmaceutical compositions comprising said crystalline forms, pharmaceutical compositions prepared from such crystalline forms, and their use as endothelin receptor antagonists. It also relates to new uses of {5-(4-bromo-phenyl)-6-[2-(5-bromo-pyrimidin-2-yloxy)-ethoxy]-pyrimidin-4-yl}-sulfamide, either alone or in combination with other active ingredients or therapeutic agents.

25 Claims, 10 Drawing Sheets

(56) References Cited

OTHER PUBLICATIONS

Bakris, G. et al., "Divergent Results Using Clinic and Ambulatory Blood Pressures; Report of a Darusentan-Resistant Hypertension Trial," Hypertension, vol. 56, pp. 824-830 (2010).
Baltatu, O. et al., "Avosentan is protective in hypertensive nephropathy at doses not causing fluid retention," Pharmacological Research, pp. 1-5 (2013).
Bolli, M. H. et al., "The Discovery of N-[5-(4-Bromophenyl)-6-[2-[(5-bromo-2-pyrimidinyl)oxy]ethoxy]-4-pyrimidinyl]-N'-propylsulfamide (Macitentan), an Orally Active, Potent Dual Endothelin Receptor Antagonist," Journal of Medicinal Chemistry, vol. 55, pp. 7849-7861 (2012); 2 parts.
Bolli, M. et al., "The Discovery of N-[5-(4-Bromophenyl)-6-[2-[(5-bromo-2-pyrimidinyl)oxy]ethoxy]-4-pyrimidinyl]-N'-propylsulfamide (Macitentan), an Orally Active, Potent Dual Endothelin Receptor Antagonist," Supporting Information, pp. 1-30.
Bolli, M., "The Discovery of Macitentan—A Standard Medicinal Chemistry Program?" Chimia, vol. 71(7/8), pp. 420-429 (2017).
Boss, C. et al., "From bosentan (Tracleer®) to macitentan (Opsumit®): The medicinal chemistry perspective," Bioorganic & Medicinal Chemistry Letters, vol. 26, pp. 3381-3394 (2016).
Bruderer, S. et al., "Absorption, distribution, metabolism, and excretion of macitentan, a dual endothelin receptor antagonist, in humans," Xenobiotica, pp. 1-10 (2012).
Burnier, M., "Update on Endothelin Receptor Antagonists in Hypertension," Current Hypertension Reports, vol. 20(51), pp. 1-7 (2018).
Calhoun, D. et al., "Triple Antihypertensive Therapy with Amlodipine, Valsartan, and Hydrochlorothiazide," Hypertension, 2009, 54, 32-39.
Chow, C. et al., "Quarter-dose quadruple combination therapy for initial treatment of hypertension: placebo-controlled, crossover, randomised trial and systematic review," Lancet, vol. 389, pp. 1035-1042 (2017).
Danaietash, P. et al., "Efficacy and Safety of Various Doses of the New Dual Endothelin Receptor Antagonist Aprocitentan in the Treatment of Hypertension," ESC Congress 2019 together with World Congress of Cardiology, 2019, 1 page.
Davenport, A. et al., "Endothelin," Pharmacological Reviews, vol. 68, pp. 357-418 (2016).
De Kanter, R. et al., "Physiologically-Based Pharmacokinetic Modeling of Macitentan: Prediction of Drug-Drug Interactions," Clin Pharmacokinet, 12 pages (2015).
Demir, D. et al., "New strategies to tackle diabetic kidney disease," Curr Opin Nephrol Hypertens, vol. 25(4), pp. 348-354 (2016).
Denolle, T. et al., "Management of resistant hypertension: expert consensus statement from the French Society of Hypertension, an affiliate of the French Society of Cardiology," Journal of Human Hypertension, vol. 30, pp. 657-663 (2016).
Egido, J. et al., "Atrasentan for the treatment of diabetic nephropathy," Expert Opinion on Investigational Drugs, 22 pages (2017).
Eirin, A. et al., "Emerging concepts for patients with treatment-resistant hypertension," Trends in Cardiovascular Medicine, pp. 1-7 (2016).
European Medicines Agency, "EMA/527460/2013 EMEA/H/C/001068; EPAR summary for the public; Exforge HCT; amlodipine / valsartan / hydrochlorothiazide," pp. 1-3 (2013).
Galiè, N. et al., "Seraphin haemodynamic substudy: the effect of the dual endothelin receptor antagonist macitentan on haemodynamic parameters and NT-proBNP levels and their association with disease progression in patients with pulmonary arterial hypertension," European Heart Journal, vol. 38, pp. 1147-1155 (2017).
Gavras, H. et al., "Malignant Hypertension Resulting from Deoxycorticosterone Acetate and Salt Excess; Role of Renin and Sodium in Vascular Changes," Circulation Research, vol. 36, pp. 300-309 (1975).
Goddard, J. et al., "Endothelin a Receptor Antagonism and Angiotensin-Converting Enzyme Inhibition Are Synergistic via an Endothelin B Receptor-Mediated and Nitric Oxide-Dependent Mechanism," Journal of the American Society of Nephrology, vol. 15, pp. 2601-2610 (2004).
Gradman, A. et al., "Combination therapy in hypertension," Journal of the American Society of Hypertension, vol. 4(1) pp. 42-50 (2010).
Griesser, U., "The Importance of Solvates," Chapter 8, Polymorphism in the Pharmaceutical Industry, pp. 211-233 (2006).
Gueneau De Mussy, P. et al., "Effects of the Dual Endothelin Receptor Antagonist Aprocitentan on Body Weight and Fluid Homeostasis in Healthy Subjects on a High Sodium Diet," Clinical Pharmacology & Therapeutics, 2021, 109 (3), 746-753.
Hunter, R. et al., "First-in-Man Demonstration of Direct Endothelin-Mediated Natriuresis and Diuresis," Hypertension, pp. 1-9 (2017).
Iglarz, M. et al., "Pharmacology of Macitentan, an Orally Active Tissue-Targeting Dual Endothelin Receptor Antagonist," The Journal of Pharmacology and Experimental Therapeutics, vol. 327(3), pp. 736-745 (2008).
Iglarz, M. et al., "Comparison of pharmacological activity of macitentan and bosentan in preclinical models of systemic and pulmonary hypertension," Life Sciences, vol. 118, pp. 333-339 (2014).
Iglarz, M. et al., "Vascular Effects of Endothelin Receptor Antagonists Depends on Their Selectivity for $ET_A$ Versus ETB Receptors and on the Functionality of Endothelial $ET_B$ Receptors," J Cardiovasc Pharmacol, vol. 66(4), pp. 332-337 (2015).
Janiak, P. et al., "Long-term blockade of angiotensin $AT_1$ receptors increases survival of obese Zucker rats," European Journal of Pharmacology, vol. 534, pp. 271-279 (2006).
Khan, W. et al., "Real-life Effectiveness, Safety, and Tolerability of Amlodipine/Valsartan or Amlodipine/Valsartan/Hydrochlorothiazide Single-pill Combination in Patients with Hypertension from Pakistan," Therapeutic Advances in Cardiovascular Disease, 2014, 8 (2), 45-55.
Kohan, D. et al., "Endothelin antagonists for diabetic and non-diabetic chronic kidney disease," British Journal of Clinical Pharmacology, vol. 76(4), pp. 573-579 (2012).
Kohan, D. et al., "Predictors of Atrasentan-Associated Fluid Retention and Change in Albuminuria in Patients with Diabetic Nephropathy," Clin J Am Soc Nephrol, vol. 10, pp. 1568-1574 (2015).
Laffin, L. et al., "Endothelin Antagonism and Hypertension: An Evolving Target," Seminars in Nephrology, vol. 35(2), pp. 168-175 (2015).
Lepist, E. et al., "Evaluation of the Endothelin Receptor Antagonists Ambrisentan, Bosentan, Macitentan, and Sitaxsentan as Hepatobiliary Transporter Inhibitors and Substrates in Sandwich-Cultured Human Hepatocytes," PLOS One, vol. 9(1), e87548, pp. 1-10 (2014).
Maguire, J. et al., "Endothelin Receptors and Their Antagonists," Seminars in Nephrology, vol. 35(2), pp. 125-136 (2015).
Mancia, G. et al., "2013 ESH/ESC Guidelines for the management of arterial hypertension; The Task Force for the management of arterial hypertension of the European Society of Hypertension (ESH) and of the European Society of Cardiology (ESC)," Journal of Hypertension, vol. 31(7), pp. 1281-1357 (2013).
Mann, J et al., "Avosentan for Overt Diabetic Nephropathy," J Am Soc Nephrol., vol. 21(3), pp. 1-19 (2010).
Mann, J. et al., "Avosentan for Overt Diabetic Nephropathy," Journal of the American Society of Nephrology, 2010, 21, 527-535.
McCormack, T. et al., "Optimising hypertension treatment: NICE/BHS guideline implementation and audit for best practice," The British Journal of Cardiology, vol. 20 (Supplement 1):S1-S15 (2013).
McMahon, G., "VEGF Receptor Signaling in Tumor Angiogenesis," The Oncologist 2000, 5 (suppl 1), 3-10.
Nielsen, E. et al., "Dual Endothelin Receptor Blockade Abrogates Right Ventricular Remodeling and Biventricular Fibrosis in Isolated Elevated Right Ventricular Afterload," PLOS One, pp. 1-18 (2016).
Pinedo, H. et al., "Translational Research: The Role of VEGF in Tumor Angiogenesis," The Oncologist, 2000, 5 (suppl 1), 1-2.
Rabelink, T. et al., "Endothelin Receptor Blockade in Patients with Diabetic Nephropathy," Contrib Nephrol., vol. 172, pp. 235-242 (2011).
Rapp, J., "Dahl Salt-Susceptible and Salt-Resistant Rats," Hypertension, vol. 4(6), pp. 753-763 (1982).
Remington, "Pharmaceutical Manufacturing," Part 5, The Science and Practice of Pharmacy, $21^{st}$ Edition, 5 pages (2005).

(56) References Cited

OTHER PUBLICATIONS

Saleh, M. et al., "Distinct Actions of Endothelin A—Selective Versus Combined Endothelin A/B Receptor Antagonists in Early Diabetic Kidney Disease," The Journal of Pharmacology and Experimental Therapeutics, vol. 338(1), pp. 263-270 (2011).

Sen, S. et al., "Renal, retinal and cardiac changes in type 2 diabetes are attenuated by macitentan, a dual endothelin receptor antagonist," Life Sciences, pp. 1-11 (2012).

Sharma, K., "Did all thiazides take undue credit of good work of chlorthalidone?" Indian Journal of Pharmacology, vol. 48(5), 3 pages (2016).

Sidharta, P. et al., "Macitentan: entry-into-humans study with a new endothelin receptor antagonist," Eur J Clin Pharmacol, 8 pages (2011).

Sidharta, P. et al., "Pharmacokinetics of the Novel Dual Endothelin Receptor Antagonist Macitentan in Subjects With Hepatic or Renal Impairment," The Journal of Clinical Pharmacology, vol. 54(3), pp. 291-300 (2013).

Sidharta, P. et al., "Clinical Pharmacokinetics and Pharmacodynamics of the Endothelin Receptor Antagonist Macitentan," Clin Pharmacokinet, vol. 54, pp. 457-471 (2015).

Sidharta, P. et al., "Single- and Multiple Dose Tolerability, Safety, Pharmacokinetics, and Pharmacodynamics of the Dual Endothelin Receptor Antagonist Aprocitentan in Healthy Adult and Elderly Subjects," Drug Design, Development and Therapy, 2019, 13, 949-964.

The Fifteenth International Conference on Endothelin, ET-15, Program and Abstract Book, 2 pages (Oct. 4-7, 2017).

Thomson Reuters, "Actelion Ltd Cardiovascular Pipeline Update Corporate Call", Final Transcript, 17 pages (Nov. 7, 2016).

Treiber, A. et al., "Macitentan Does Not Interfere with Hepatic Bile Salt Transport," J Pharmacol Exp Ther, vol. 350, pp. 130-143 (2014).

Treiber, A. et al., "The metabolism of the dual endothelin receptor antagonist macitentan in rat and dog," Xenobiotica, pp. 1-15 (2015).

Trensz, F., "Pharmacology of ACT-132577 (aprocitentan); A dual endothelin receptor antagonist for the treatment of resistant hypertension," ET-15 Conference, 19 pages (Oct. 5, 2017).

Trensz, F., "Pharmacological Characterization of Aprocitentan, a Dual Endothelin Receptor Antagonist, Alone and in Combination with Blockers of the Renin Angiotensin System, in Two Models of Experimental Hypertensions," J Pharmacol Exp Ther, vol. 368, pp. 462-473 (2019); Supplemental Figures, 6 pages.

Tullos, N. et al., "Chronic blockade of endothelin A and B receptors using macitentan in experimental renovascular disease," Nephrol Dial Transplant, vol. 0, pp. 1-10 (2014).

Valero-Munoz, M. et al., "Dual Endothelin-A/Endothelin-B Receptor Blockade and Cardiac Remodeling in Heart Failure With Preserved Ejection Fraction," Circ Heart Fail., pp. 1-9 (2016); Supplemental Material, 23 pages.

Vercauteren, M. et al., "Endothelin ETA Receptor Blockade, by Activating $ET_B$ Receptors, Increases Vascular Permeability and Induces Exaggerated Fluid Retentions," The Journal of Pharmacology and Experimental Therapeutics, vol. 361, pp. 322-333 (2017); Supplementary material, 2 pages.

Verweij, P. et al., "Randomized Dose-response Study of the New Dual Endothelin Receptor Antagonist Aprocitentan in Hypertension," Hypertension, 2020, 75, 956-965.

Supplemental Information for: Verweij, P. et al., "Randomized Dose-response Study of the New Dual Endothelin Receptor Antagonist Aprocitentan in Hypertension," Hypertension, 2020, 75, 956-965, 15 pages, retrieved on Nov. 9, 2022, from: https://www.ahajournals.org/doi/suppl/10.1161/HYPERTENSIONAHA.119.14504.

Wald, D. et al., "Combination Therapy Versus Monotherapy in Reducing Blood Pressure: Meta-analysis on 11,000 Participants from 42 Trials," The American Journal of Medicine, vol. 122(3), pp. 290-300, (2009).

Wan, X. et al., "A promising choice in hypertension treatment: Fixed-dose combinations," Asian Journal of Pharmaceutical Sciences, vol. 9, pp. 1-7 (2014).

Weber, M. et al., "A selective endothelin-receptor antagonist to reduce blood pressure in patients with treatment-resistant hypertension: a randomised, double-blind, placebo-controlled trial," Lancet, vol. 374, pp. 1423-1431 (2009).

Weber, M. et al., "Clinical Practice Guidelines for the Management of Hypertension in the Community a Statement by the American Society of Hypertension and the International Society of Hypertension," The Journal of Clinical Hypertension, vol. 16(1), pp. 14-26 (2014).

Whelton, P. et al., "2017 High Blood Pressure Clinical Practice Guideline," Hypertension, 481 pages (2017).

Zhang, J. et al., "Pharmacokinetic study of ACT-132577 in rat plasma by ultra performance liquid chromatography-tandem mass spectrometry," Int J Clin Exp Med, vol. 8(10), pp. 18420-18426 (2015).

U.S. Appl. No. 18/929,609, filed Oct. 28, 2024, Bellet et al.

* cited by examiner

Fig. 1, Form A
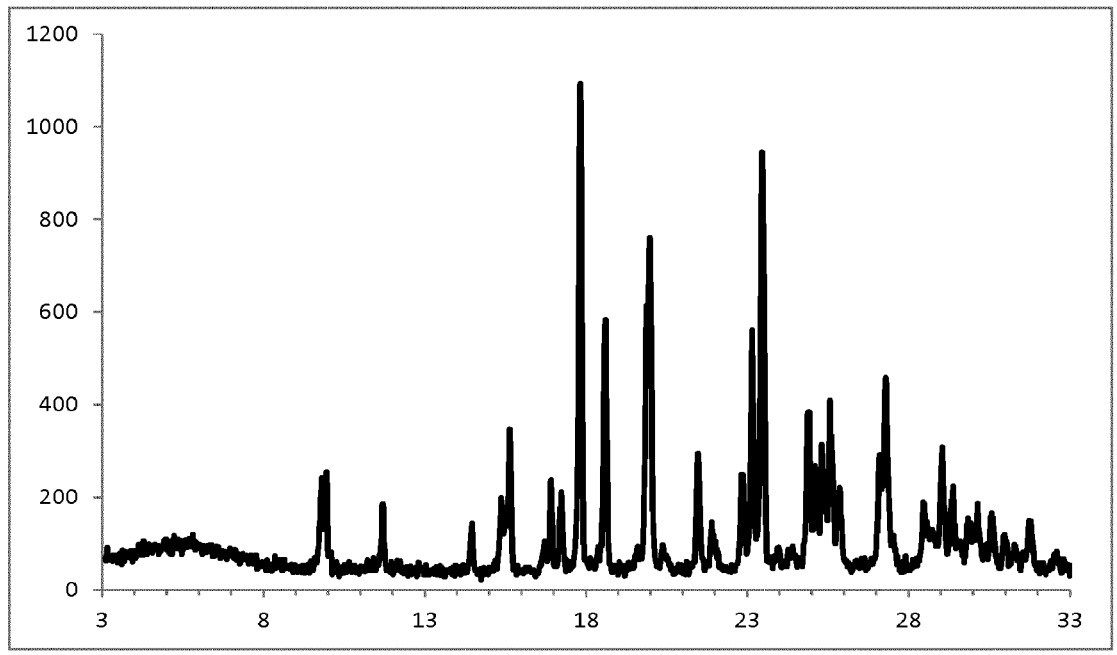
Fig. 2, Form B
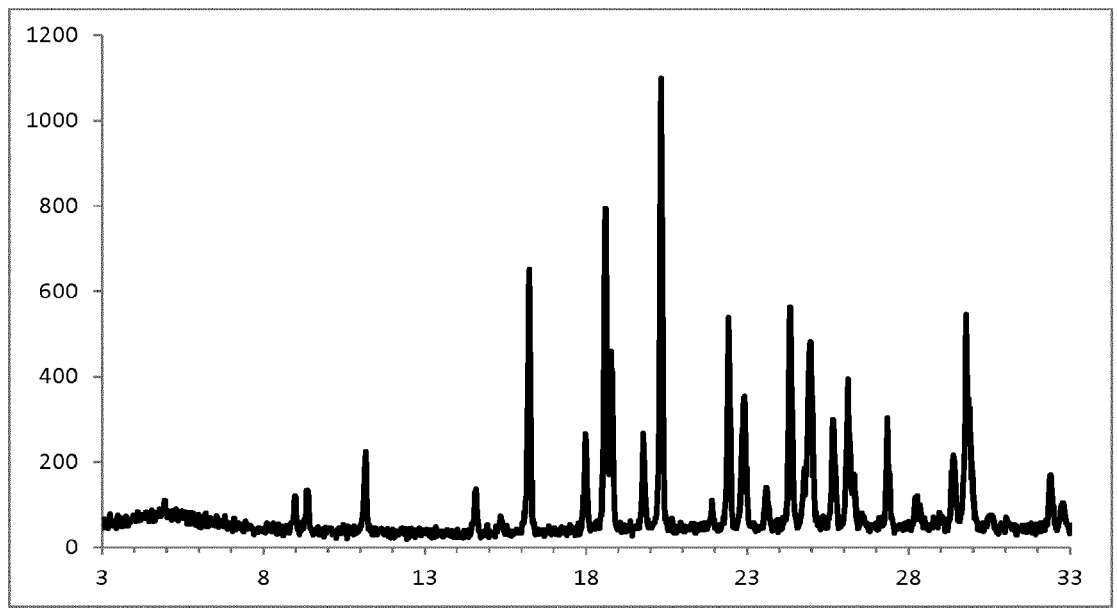

Fig. 3, Form C
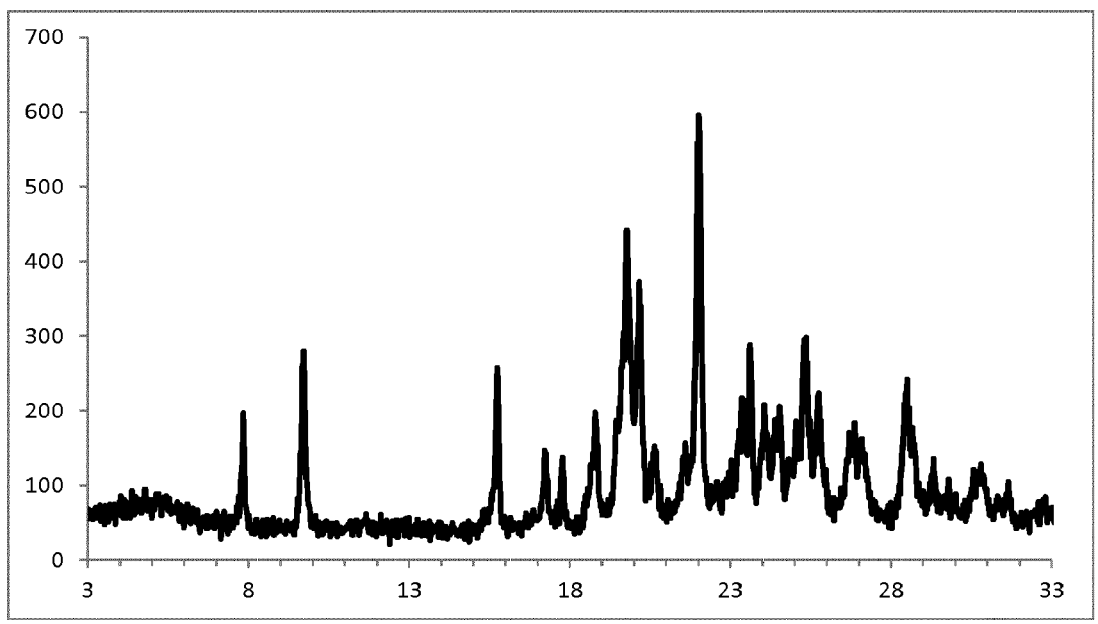
Fig. 4, Form D
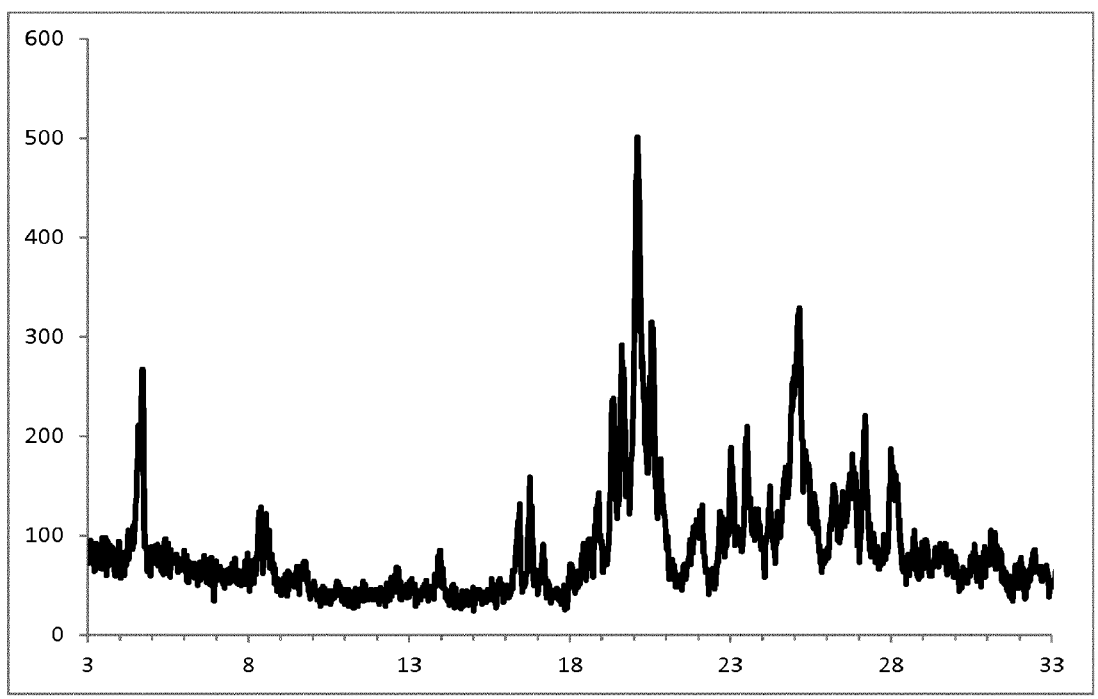

Fig. 5, Form E
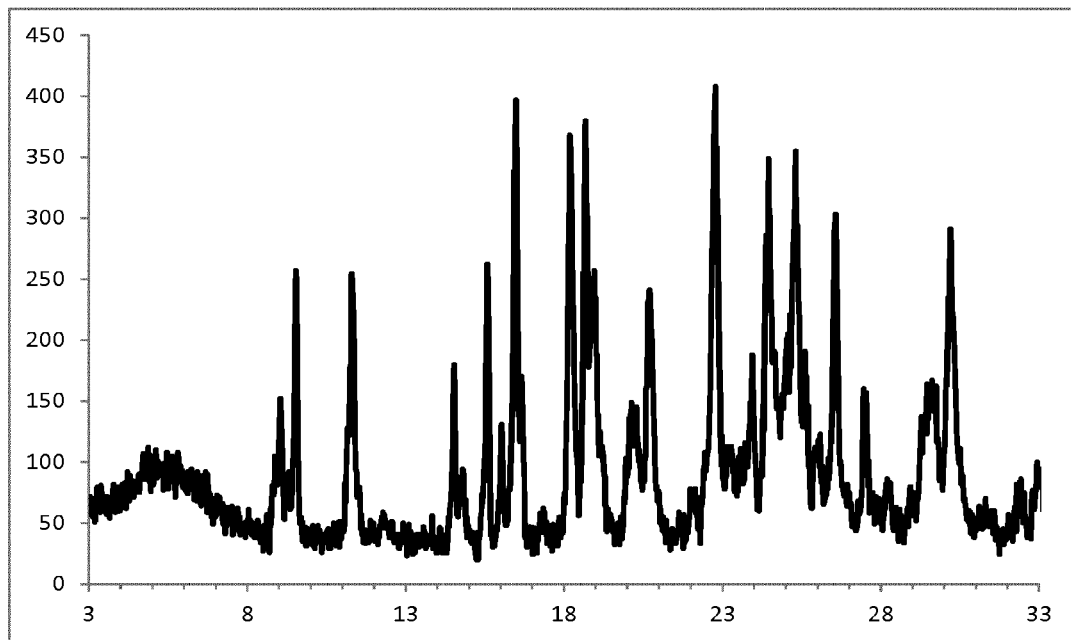
Fig. 6, Form J
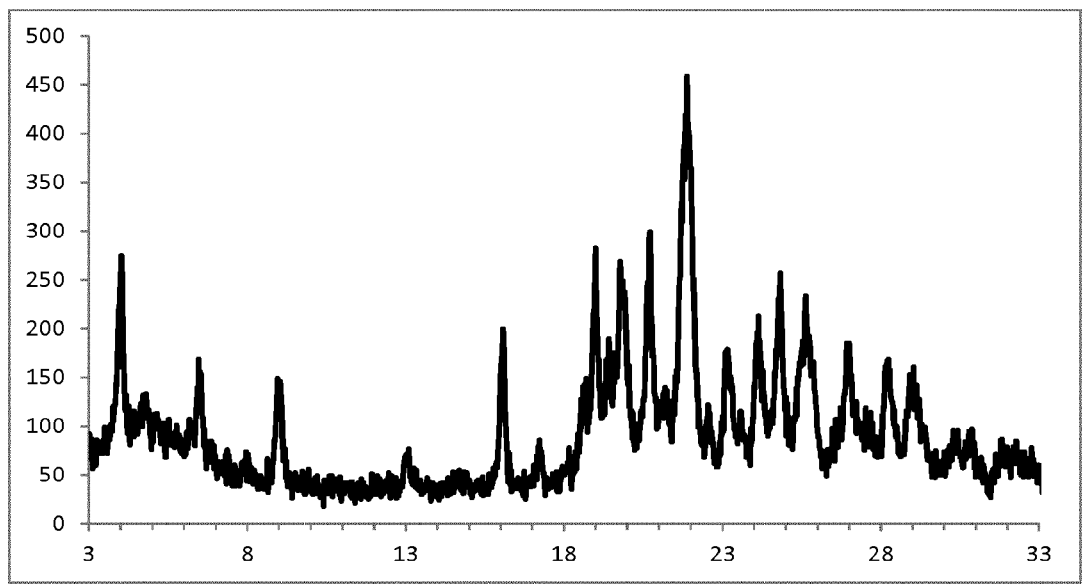

Fig. 7, Form K
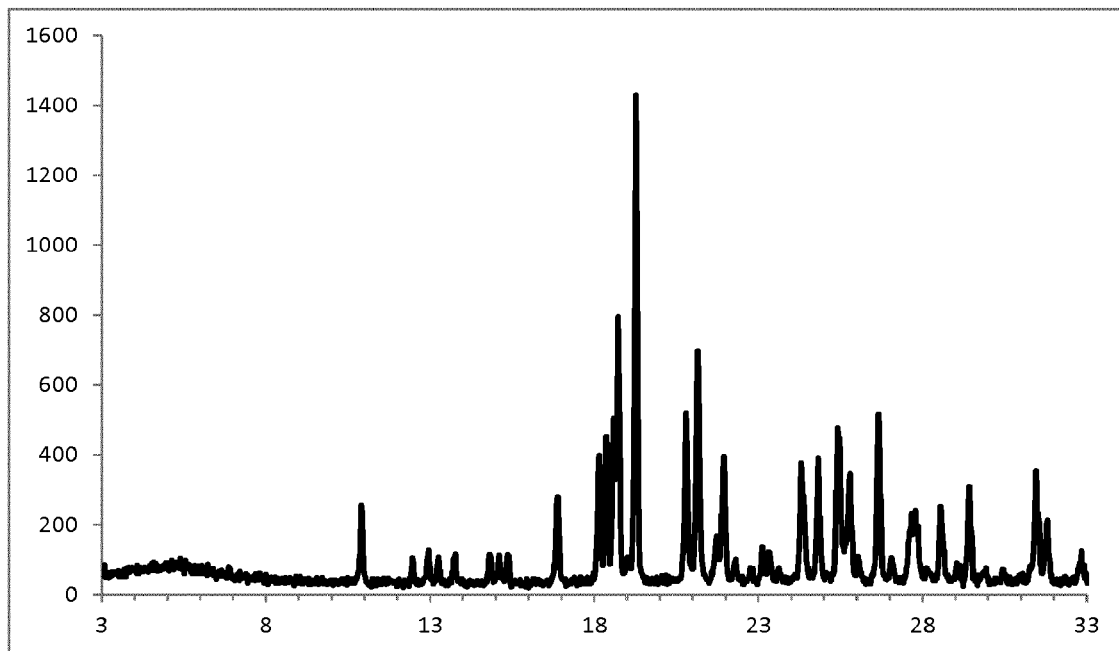
Fig. 8, Form L
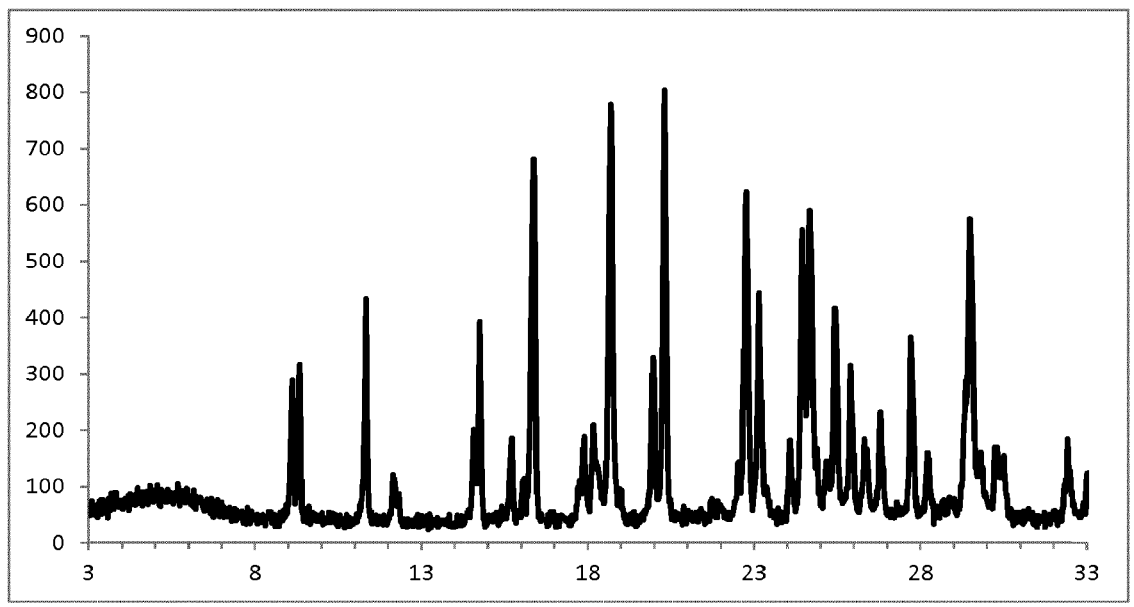

CRYSTALLINE FORMS OF A 4-PYRIMIDINESULFAMIDE DERIVATIVE APROCITENTAN

CROSS REFERENCE TO RELATED APPLICATIONS

This application is a continuation of U.S. patent application Ser. No. 17/146,801 filed on Jan. 12, 2021, which is a continuation of U.S. patent application Ser. No. 16/489,194 filed on Aug. 27, 2019, now issued as U.S. Pat. No. 10,919,881, which is a National Stage Entry under 35 U.S.C. § 371 claiming benefit of PCT Application No. PCT/EP2018/054627, filed on Feb. 26, 2018, which claims the benefit of PCT Application Nos. PCT/EP2017/054489, filed on Feb. 27, 2017, and PCT/EP2017/061487, filed on May 12, 2017, the contents of each of which are incorporated herein by reference.

The present invention concerns novel crystalline forms of {5-(4-bromo-phenyl)-6-[2-(5-bromo-pyrimidin-2-yloxy)-ethoxy]-pyrimidin-4-yl}-sulfamide (hereinafter also referred to as "COMPOUND"), processes for the preparation thereof, pharmaceutical compositions comprising said crystalline forms, pharmaceutical compositions prepared from such crystalline forms, and their use as endothelin receptor inhibitors and endothelin receptor antagonists. It also relates to uses of the COMPOUND for treating particular diseases or disorders, either alone or in combination with other active ingredients or therepautic agents.

Aprocitentan, {5-(4-bromo-phenyl)-6-[2-(5-bromo-pyrimidin-2-yloxy)-ethoxy]-pyrimidin-4-yl}-sulfamide has the formula I

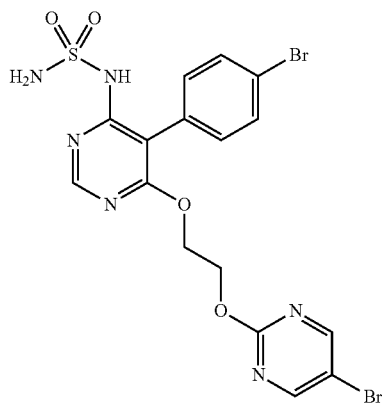

I

Aprocitentan, also known under the name ACT-132577, is an endothelin receptor inhibitor and useful as endothelin receptor antagonist. The compound of formula I is a member of a structural family that was previously generically disclosed in WO 02/053557. In particular, the compound of formula I, while showing endothelin receptor antagonist activity, exhibits in vivo a much longer half-life and a much shorter clearance in comparison to corresponding alkylated derivatives. This makes the compound of formula I particularly suitable for long-acting pharmaceutical compositions, as disclosed in WO 2009/024906. Certain manufacturing processes relating to aprocitentan are disclosed in WO2015/121397.

Because of its ability to inhibit the endothelin binding, COMPOUND can be used for treatment of endothelin related diseases which are associated with an increase in vasoconstriction, proliferation or inflammation due to endothelin. Examples of such endothelin related diseases are hypertension, pulmonary hypertension, coronary diseases, cardiac insufficiency, renal and myocardial ischemia, renal failure, cerebral ischemia, dementia, migraine, subarachnoidal hemorrhage, Raynaud's syndrome, digital ulcers and portal hypertension. They can also be used in the treatment or prevention of chronic kidney disease (CKD), diabetes, diabetic nephropathy, diabetic retinopathy, diabetic vasculopathy, chronic heart failure and diastolic dysfunction. they can further be used in the treatment or prevention of atherosclerosis, restenosis after balloon or stent angioplasty, inflammation, stomach and duodenal ulcer, cancer, melanoma, prostate cancer, prostatic hypertrophy, erectile dysfunction, hearing loss, amaurosis, chronic bronchitis, asthma, pulmonary fibrosis, gram negative septicemia, shock, sickle cell anemia, glomerulonephritis, renal colic, glaucoma, connective tissue diseases, therapy and prophylaxis of diabetic complications, complications of vascular or cardiac surgery or after organ transplantation, complications of cyclosporin treatment, pain, hyperlipidemia as well as other diseases, presently known to be related to endothelin.

According to the 2014 American Society of Hypertension and International Society of Hypertension joint statement [Weber et al., "Clinical Practice Guidelines for the Management of Hypertension in the Community. A Statement by the American Society of Hypertension and the International Society of Hypertension." J Clin Hypertens (2014), 16(1), 14-26], the 2013 European Society of Hypertension and European Society of Cardiology joint guideline [Mancia et al, J. Hypertens. (2013), 31, 1281 1357], as well as several national guidelines [Denolle et al., J Hum Hypertens. (2016), 30(11), 657-663; McCormack et al., Br J Cardiol (2013), 20 (suppl 1), S1-S16], resistant hypertension (rHT) (or difficult to treat hypertension) is defined as uncontrolled blood pressure (BP) (i.e., failure to lower BP to a pre-defined threshold) despite concurrent administration of three antihypertensive therapies of different pharmacological classes at maximal or optimal doses, including a diuretic. Thus, resistant hypertension patients include patients whose blood pressure is controlled with use of more than three medications. That is, patients whose blood pressure is controlled but require four or more medications to do so should be considered resistant to treatment (see e.g. Mancia et al, J. Hypertens. (2013)).

Clinical studies have shown that endothelin receptor antagonists (ERAs) may have significant treatment effect in patients suffering from hypertension and/or renal disease. However, therapeutic benefit needs to be weighted against potential side effects, such as the potential risk of teratogenic activity. In addition, both, selective $ET_A$-antagonists and dual antagonists of both the $ET_A$ and $ET_B$ receptor, may cause fluid retention, a common side effect associated with many previously studied ERAs and sometimes (e.g. if not manageable with diuretics) leading to exaggerated major adverse cardiac events such as heart failure or death. Whereas the risk-benefit balance is in most cases in favor of treatment with an ERA for indications such as pulmonary hypertension (as reflected in the past by successive market approvals e.g. for the ERAs the dual antagonists bosentan and macitentan, the $ET_A$-selective antagonist ambrisentan), ERAs have no role in the management of primary hypertension (Laffin et al. Seminars in Nephrology 2015, 35, 168-175), and side effects such as fluid retention may remain an issue when a potential treatment of rHT, chronic kidney disease or other hypertension related diseses with an ERA is considered.

The $ET_A$-selective endothelin receptor antagonist darusentan has been in development for the treatment of rHT (Bakris et al., Hypertension 2010, 56, 824-830, see also WO2007/098390). In a 14 week phase 3 trial in patients with rHT, it demonstrated efficacy on the reduction of ambulatory blood pressure, but failed to show significant treatment effect on the primary endpoint systolic blood pressure. Patients were eligible to participate if they had treatment resistant hypertension (systolic blood pressure of higher than 140 mm Hg) despite treatment with three or more antihypertensive drugs from different drug classes, including a diuretic, at optimized doses. A minimum dose of 25 mg per day of hydrochlorothiazide (or its equivalent for other thiazide diuretic drugs) was required. Even though during the trial diuretic therapy could be intensified at the discretion of the investigators to manage fluid retention, the most frequent adverse event associated with darusentan was fluid retention/edema at 28% versus 12% in each of the other groups. More patients withdrew because of adverse events on darusentan as compared with placebo.

WO2016/073846 provides a comprehensive summary of ERAs tested for various indications including chronic kidney disease (CKD) and rHT. Similarly to the observations made for darusentan mentioned above, also the $ET_A$-selective ERA avosentan, in a trial that investigated the use of avosentan to reduce proteinuria in patients with diabetes, showed significant treatment effect, associated with a significantly increased discontinuation of trial medications due to adverse events, predominantly related to fluid overload and congestive heart failure. The trial was terminated prematurely, and the authors conclude that "it may be that at dosages of 25 to 50 mg, avosentan is less selective for the $ET_A$ receptor and thus caused sodium and water retention and peripheral vasodilation with a potential fluid shift from the intravascular to extravascular space. The assumption of $ET_B$ receptor blockade with higher dosages of avosentan is further supported by data that showed a natriuretic effect of selective $ET_A$ receptor blockade in people who were treated with ACEIs (Mann et al., J Am Soc Nephrol. 2010, 21(3): 527-535." WO2016/073846 provides further examples where fluid retention may have led to increased side effects for the ERAs bosentan, tezosentan, ambrisentan, and atrasentan. WO2016/073846 concludes in proposing a method of treating CKD with an ERA, especially with the ETA-selective ERA atrasentan, using predictors of fluid retention; said method comprising the determination of a risk of fluid retention if an ERA were administered to the subject; and administering the ERA to the subject if the risk is at an acceptable level.

Preclinical and clinical data suggest that the $ET_A$-selective antagonists sitaxentan and ambrisentan pose a greater risk of fluid retention than the dual ERAs bosentan and macitentan (Vercauteren et al., JPET 2017, 361, 322-333). On the other hand, pre-clinical data showed that the synergistic effect on blood pressure of an $ET_A$-selective ERA in combination with the ACE inhibitor enalapril was abolished by simultaneous blockade of the $ET_B$-receptor (Goddard et al., J.Am.Soc.Nephrol. 2004, 15, 2601-2610). It has been shown in a phase 2 trial that aprocitentan, an ERA resulting in effective dual blockade of the endothelin receptors, may result in efficacious control of blood pressure in subjects having essential hypertension. (aprocitentan was administered as monotherapy, i.e. without background anti-hypertensive therapy) (Actelion Pharmaceuticals Ltd, press release May 22, 2017). Even though some indications of potential fluid retention were observed (e.g. increased body weight at higher doses, dose related decrease in the hemoglobin concentration, four cases of peripheral edema at higher doses), the overall frequency of adverse events was similar to those observed in the placebo group. Thus, different from the methods of WO2016/073846 no risk assessment and/or dose reduction to mitigate side effects related to fluid retention may be required for aprocitentan when used in the treatment of hypertension related diseases, especially resistant hypertension. Thus, aprocitentan may have a different pharmacological profile than the predominantly ETA-selective antagonists so far tested in resistant hypertension or chronic kidney disease in diabetic and non-diabetic patients.

It has now been found that certain crystalline forms of COMPOUND may under certain conditions be found. Said crystalline forms of COMPOUND are novel and may have advantageous properties in view of the potential use of COMPOUND as active pharmaceutical ingredient. Such advantages may include better flow properties; less hygroscopicity; better reproducibiliy in manufacturing (for example better filtration parameters, better reproducibility of formation, and/or better sedimentation); and/or defined morphology. Such crystalline forms of COMPOUND may be particularly suitable in a process of manufacturing certain pharmaceutical compositions. It has also been found that COMPOUND or a pharmaceutically acceptable salt thereof is particularly useful to treat certain disorders, in particular when used in combination with other active ingredients or therepeutic agents

DESCRIPTION OF THE FIGURES

FIG. 1 shows the X-ray powder diffraction diagram of COMPOUND in a crystalline form A, e.g. as obtained from Example 1. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-33° 2theta with relative intensity larger then 10% are reported): 9.8° (18%), 9.9° (18%), 11.7° (14%), 14.5° (10%), 15.4° (14%), 15.6° (29%), 16.9° (19%), 17.2° (16%), 17.8° (100%), 18.6° (50%), 19.9° (54%), 20.0° (67%), 21.5° (24%), 21.9° (10%), 22.8° (18%), 23.2° (49%), 23.5° (83%), 24.9° (32%), 25.1° (20%), 25.3° (24%), 25.6° (33%), 25.9° (16%), 27.1° (23%), 27.3° (39%), 28.5° (13%), 29.0° (23%), 29.4° (15%), 30.1° (12%) and 30.6° (10%).

FIG. 2 shows the X-ray powder diffraction diagram of a dichloromethane solvate of the COMPOUND in a crystalline form B, e.g. as obtained from Example 2. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-33° 2theta with relative intensity larger then 10% are reported): 11.2° (16%), 16.2° (57%), 18.0° (21%), 18.6° (71%), 18.8° (36%), 19.8° (19%), 20.3° (100%), 22.4° (45%), 22.9° (28%), 24.3° (44%), 24.8° (11%), 25.0° (41%), 25.7° (22%), 26.1° (31%), 27.4° (20%), 29.4° (16%), 29.8° (38%) and 32.4° (12%).

FIG. 3 shows the X-ray powder diffraction diagram of COMPOUND in a crystalline form C, e.g. as obtained from Example 3. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-33° 2theta with relative intensity larger then 10% are reported): 7.8° (23%), 9.7° (42%), 15.7° (37%), 17.2° (16%), 17.8° (15%), 18.8° (26%), 19.8° (71%), 20.1° (51%), 20.6° (15%), 21.6° (15%), 22.0° (100%), 23.4° (27%), 23.6° (40%), 24.1° (23%), 24.5° (16%), 25.1° (13%), 25.3° (39%), 25.7° (28%), 26.8° (19%), 27.1° (16%), 28.5° (31%), 30.8° (13%) and 30.8° (13%).

FIG. 4 shows the X-ray powder diffraction diagram of COMPOUND in a crystalline form D, e.g. as obtained from Example 4. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-33° 2theta with relative intensity larger then 10% are reported): 4.6° (27%), 8.4° (15%), 8.6° (11%), 16.4° (17%), 16.8° (26%), 17.2° (10%), 18.6° (11%), 18.9° (18%), 19.3° (40%), 19.6° (45%), 20.1° (100%), 20.6° (55%), 20.8° (26%), 22.0° (10%), 22.7° (14%), 23.0° (24%), 23.5° (32%), 23.8° (12%), 24.2° (17%), 24.7° (20%), 25.1° (55%), 25.4° (22%), 25.6° (14%), 26.2° (16%), 26.8° (17%), 27.2° (28%), 28.1° (21%) and 28.1° (19%).

FIG. 5 shows the X-ray powder diffraction diagram of an acetonitrile solvate of the COMPOUND in a crystalline form E, e.g. as obtained from Example 5. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-33° 2theta with relative intensity larger then 10% are reported): 9.0° (21%), 9.5° (56%), 11.3° (61%), 14.5° (41%), 14.8° (15%), 15.6° (47%), 16.0° (26%), 16.5° (100%), 18.2° (84%), 18.7° (73%), 18.9° (56%), 20.2° (20%), 20.7° (56%), 22.8° (96%), 23.9° (22%), 24.5° (70%), 25.3° (77%), 25.6° (29%), 26.0° (14%), 26.6° (66%), 27.5° (27%), 29.6° (31%), 30.2° (66%) and 33.0° (13%).

FIG. 6 shows the X-ray powder diffraction diagram of COMPOUND in a crystalline form J, e.g. as obtained from Example 6. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-33° 2theta with relative intensity larger then 10% are reported): 4.0° (44%), 4.7° (14%), 6.5° (23%), 9.0° (27%), 16.1° (40%), 17.2° (11%), 18.7° (22%), 19.0° (58%), 19.4° (28%), 19.8° (46%), 20.7° (57%), 21.2° (17%), 21.9° (100%), 22.6° (14%), 23.2° (23%), 24.1° (37%), 24.8° (40%), 25.6° (42%), 27.0° (29%), 28.2° (27%), 29.0° (20%), 30.3° and 30.8° (10%).

FIG. 7 shows the X-ray powder diffraction diagram of a dimethylsulfoxide solvate of the COMPOUND in a crystalline form K, e.g. as obtained from Example 7. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-33° 2theta with relative intensity larger then 10% are reported): 10.9° (16%), 16.9° (18%), 18.2° (26%), 18.4° (30%), 18.6° (29%), 18.7° (55%), 19.3° (100%), 20.8° (35%), 21.2° (47%), 21.9° (26%), 24.3° (21%), 24.8° (24%), 25.4° (29%), 25.8° (22%), 26.7° (34%), 27.7° (13%), 27.8° (14%), 28.6° (15%), 29.4° (18%), 31.5° (23%) and 31.8° (12%).

FIG. 8 shows the X-ray powder diffraction diagram of an ethanol solvate of the COMPOUND in a crystalline form L, e.g. as obtained from Example 8. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-33° 2theta with relative intensity larger then 10% are reported): 9.1° (31%), 9.3° (34%), 11.3° (49%), 12.2° (10%), 14.6° (17%), 14.8° (46%), 15.7° (16%), 16.1° (10%), 16.4° (80%), 17.9° (17%), 18.2° (19%), 18.7° (96%), 20.0° (38%), 20.3° (100%), 22.6° (11%), 22.8° (76%), 23.2° (50%), 24.10 (14%), 24.5° (56%), 24.7° (68%), 25.4° (46%), 25.9° (32%), 26.4° (14%), 26.8° (22%), 27.7° (38%), 28.2° (12%), 29.7° (11%), 29.5° (64%), 29.8° (14%), 30.3° (14%), 30.5° (13%) and 32.4° (16%).

For avoidance of any doubt, the above-listed peaks describe the experimental results of the X-ray powder diffraction shown in FIG. 1 to FIG. 8. It is understood that, in contrast to the above peak list, only a selection of characteristic peaks is required to fully and unambiguously characterize of the COMPOUND in the respective crystalline form of the present invention.

In the X-ray diffraction diagrams of FIG. 1 to FIG. 8 the angle of refraction 2theta (2θ) is plotted on the horizontal axis and the counts on the vertical axis.

Figure 9:
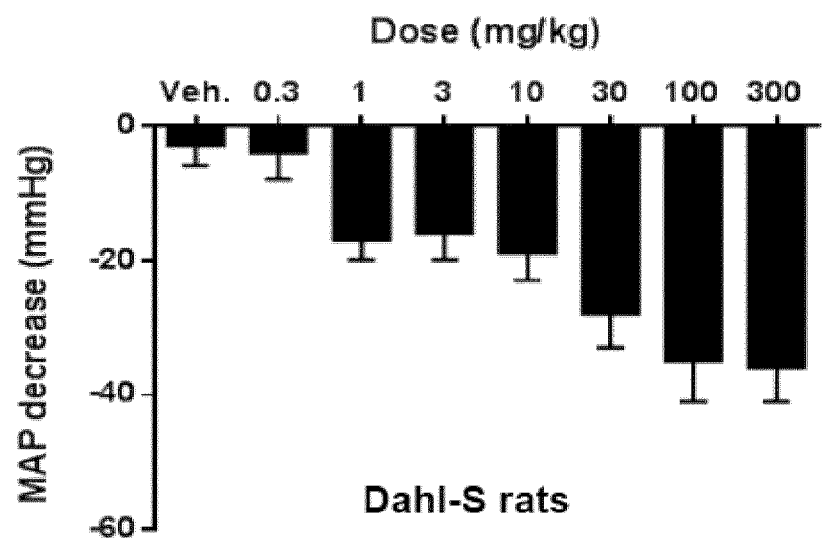

FIG. 9 shows the acute effects of COMPOUND on mean arterial blood pressure ("MAP") in conscious, male hypertensive Dahl salt sensitive rats.

Figure 10:
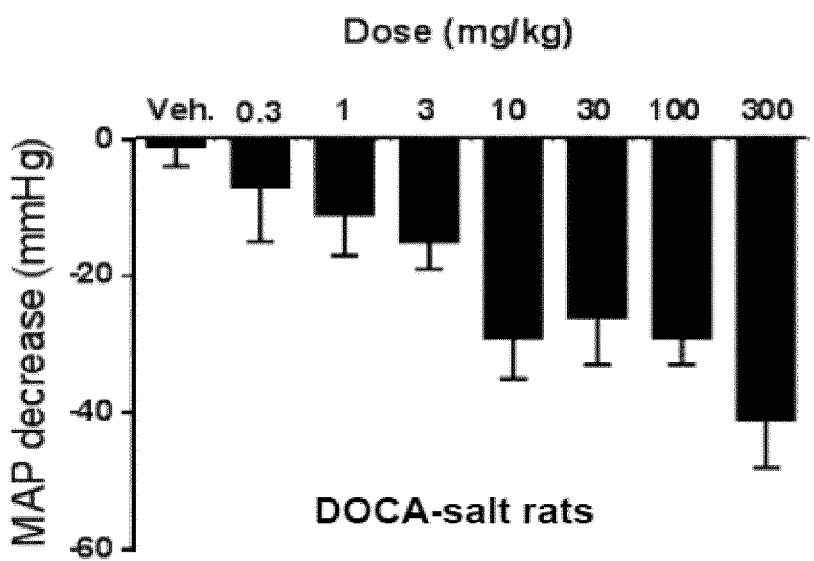

FIG. 10 shows the acute effects of COMPOUND on MAP in conscious, male hypertensive deoxycorticosterone acetate salt rats.

Figure 11:
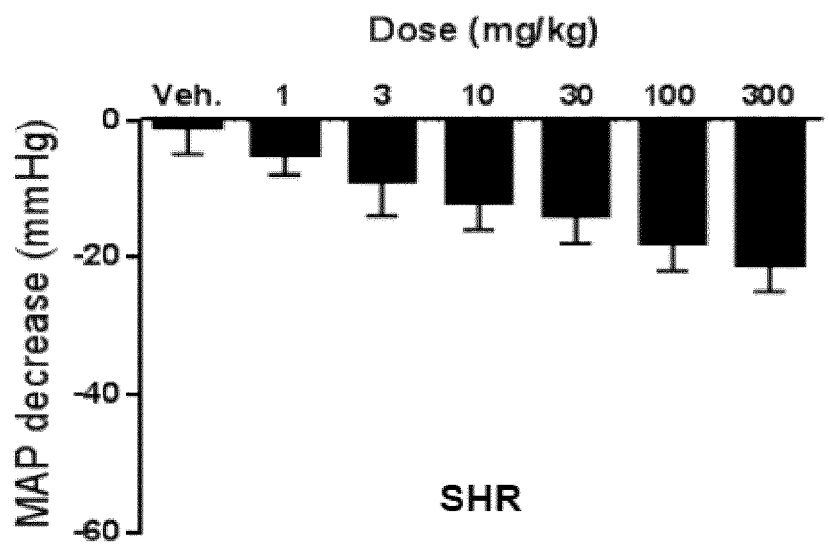

FIG. 11 shows the acute effects of COMPOUND on MAP in conscious, male spontaneaously hypertensive rats.

Figure 12:
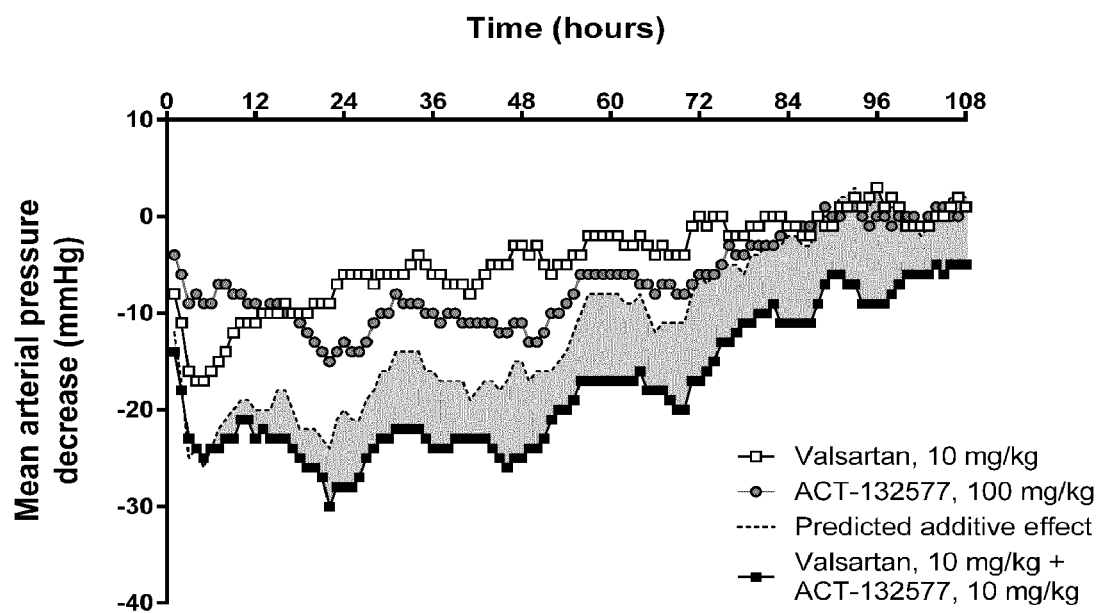

FIG. 12 shows the acute effects of COMPOUND, used alone or in combination with valsartan, on MAP in conscious, male spontaneaously hypertensive rats.

Figure 13:
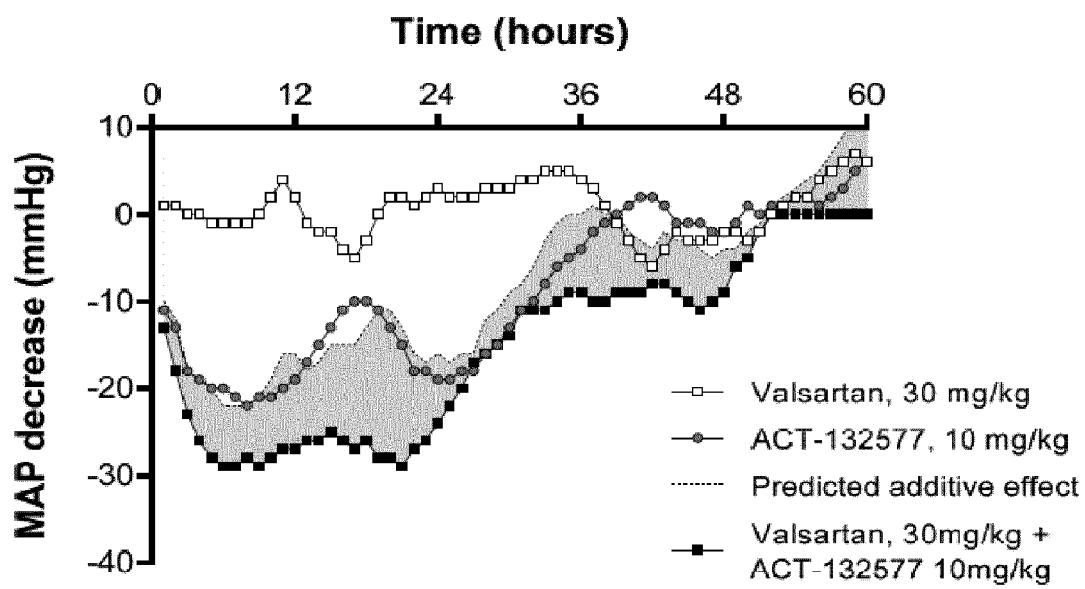

FIG. 13 shows the acute effects of COMPOUND, used alone or in combination with valsartan, on MAP in conscious, male hypertensive deoxycorticosterone acetate salt rats.

Figure 14:
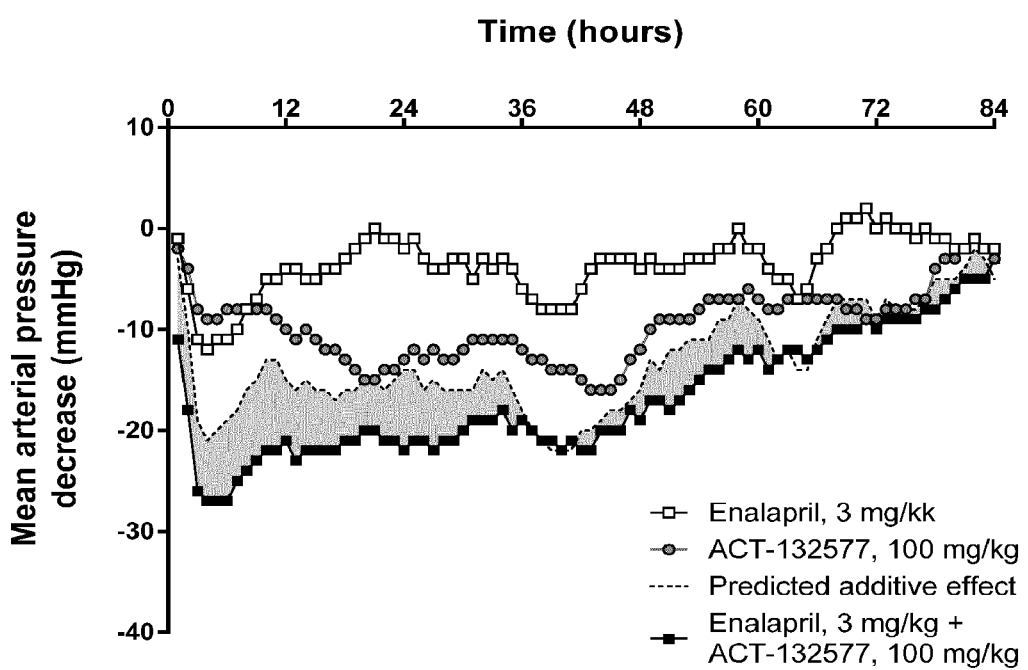

FIG. 14 shows the acute effects of COMPOUND, used alone or in combination with enalapril, on MAP in conscious, male spontancaously hypertensive rats.

Figure 15:
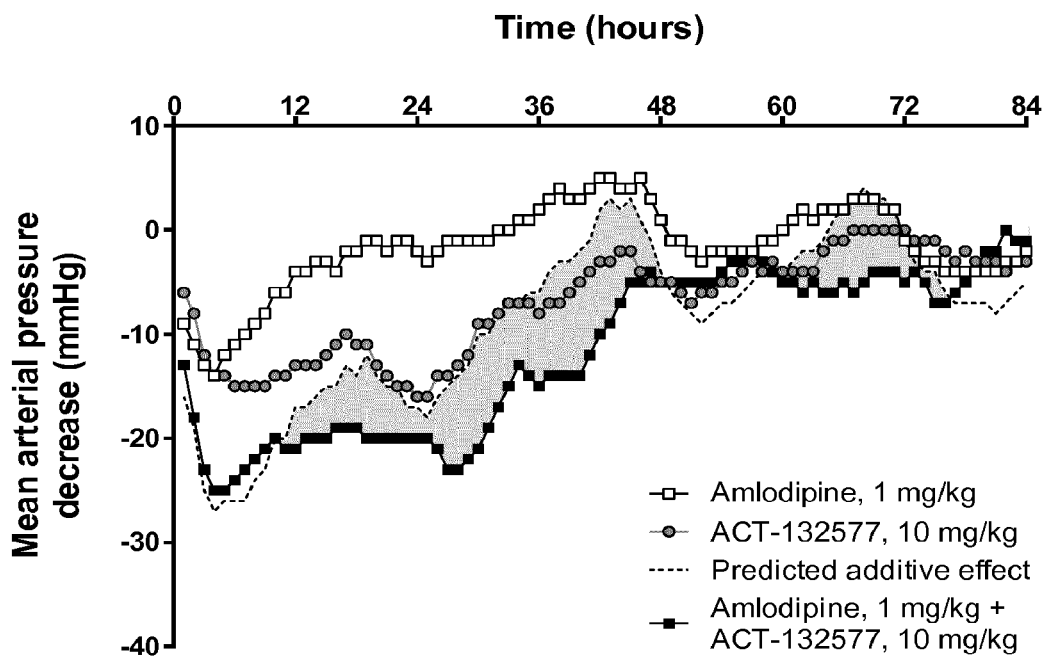

FIG. 15 shows the acute effects of COMPOUND, used alone or in combination with amlodipine, on MAP in conscious, male hypertensive deoxycorticosterone acetate salt rats.

Figure 16:
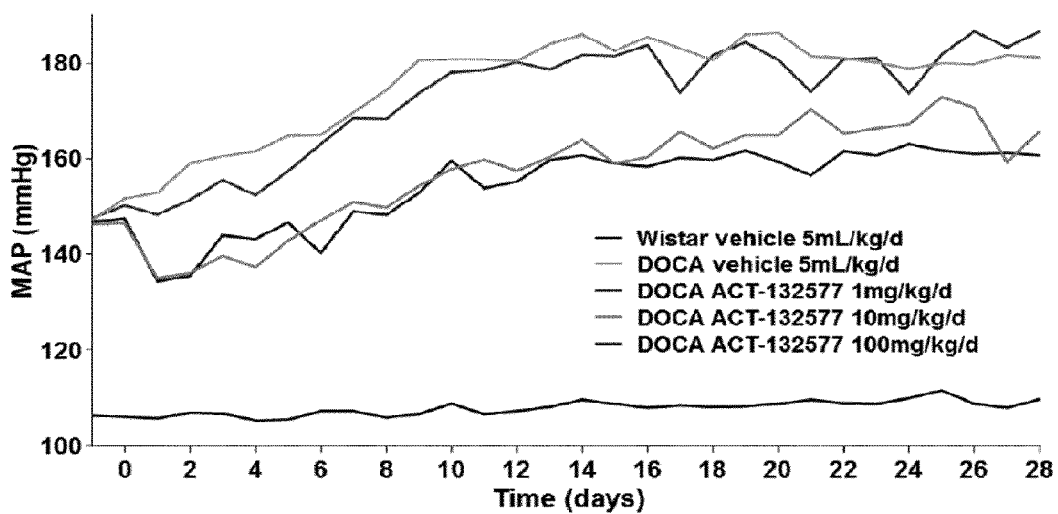

FIG. 16 shows the effects of chronic oral administration of COMPOUND on MAP in conscious, male hypertensive deoxycorticosterone acetate salt rats.

Figure 17:
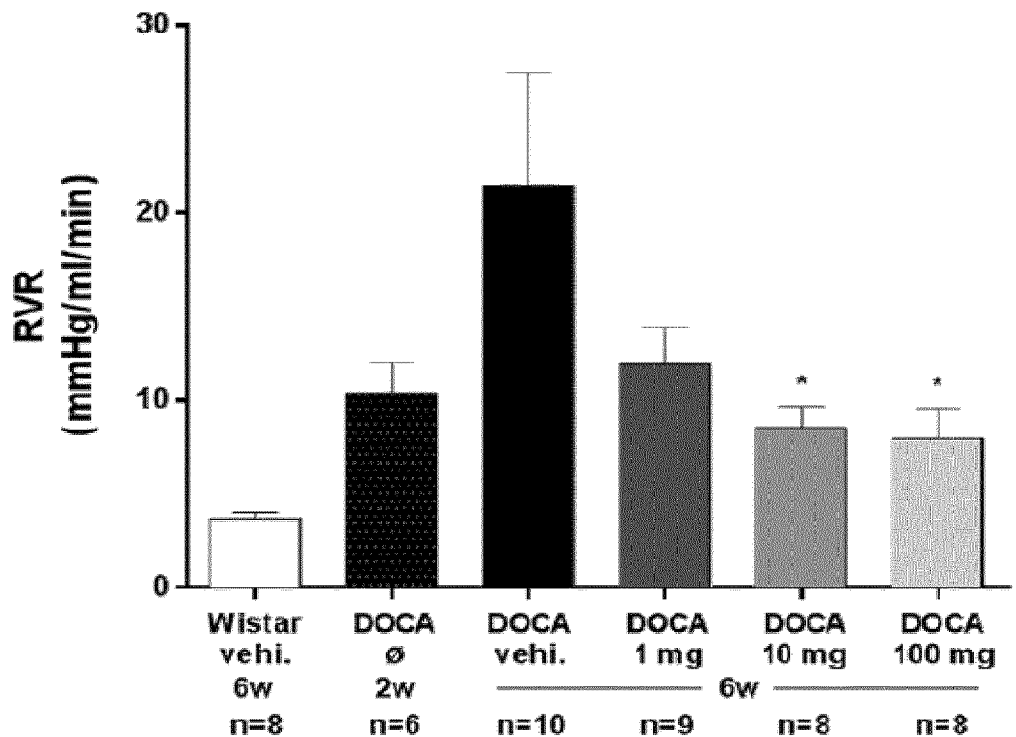

FIG. 17 shows the effects of chronic oral administration of COMPOUND on renal vascular resistance in conscious, male hypertensive deoxycorticosterone acetate salt rats.

Figure 18:
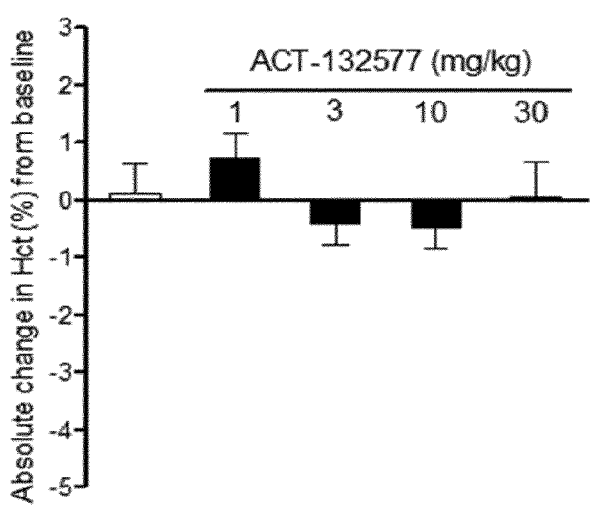

FIG. 18 shows the effects of a single dose oral administration of COMPOUND on haematocrit (Hct) male Wistar rats.

Figure 19:
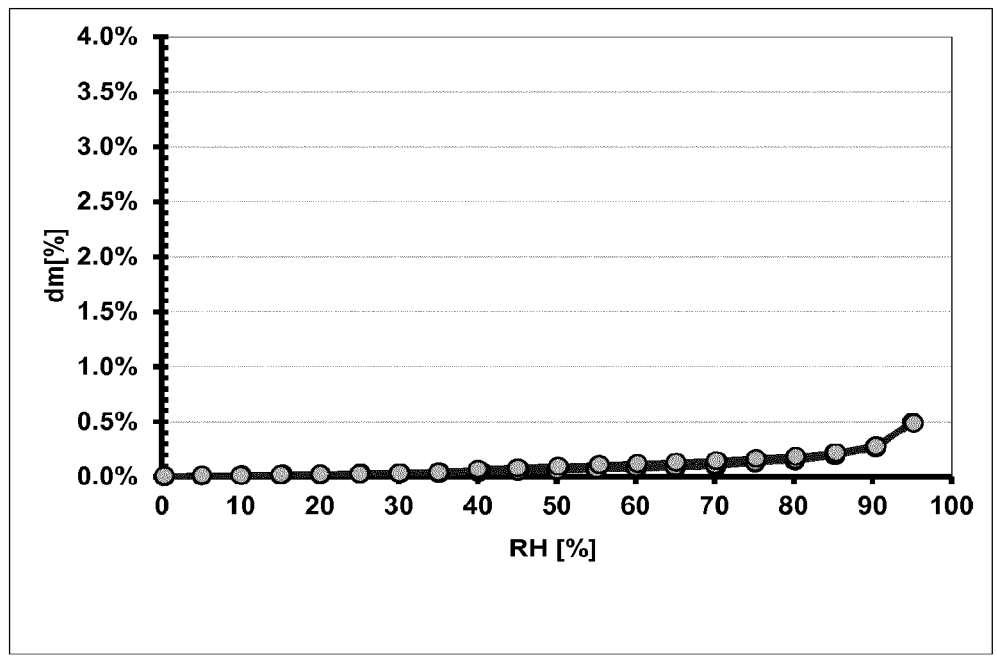

FIG. 19 shows the gravimetric vapour sorption diagram of COMPOUND in a crystalline form A as obtained from Example 1.

Figure 20:
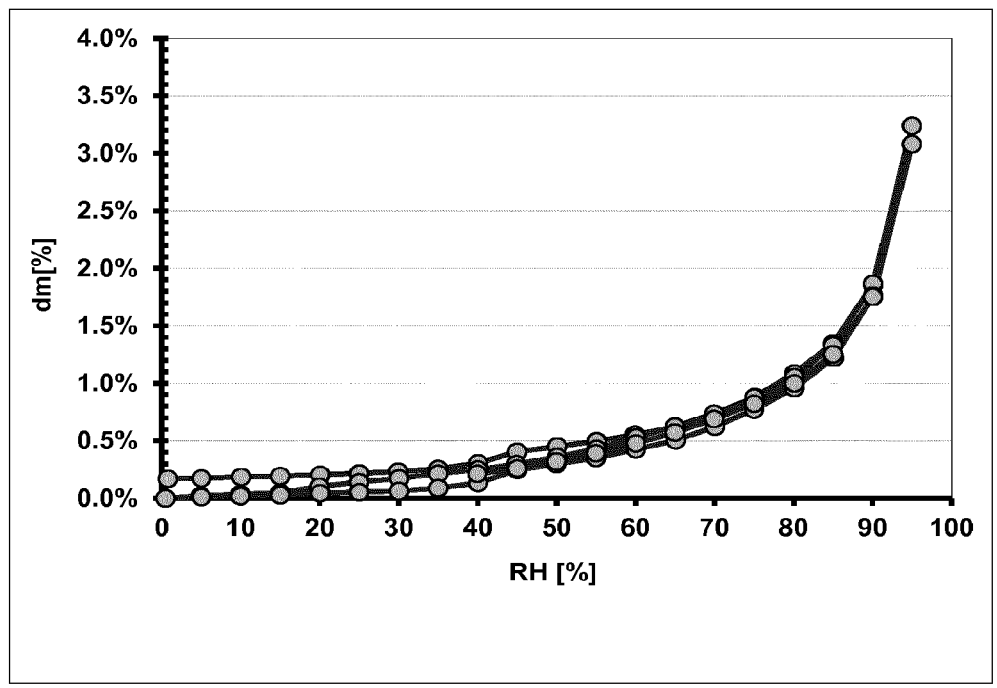

FIG. 20 shows the gravimetric vapour sorption diagram of COMPOUND in a crystalline form C as obtained from Example 3.

DETAILED DESCRIPTION OF THE INVENTION

1) A first embodiment of the invention relates to crystalline forms of the COMPOUND {5-(4-bromo-phenyl)-6-[2-

(5-bromo-pyrimidin-2-yloxy)-ethoxy]-pyrimidin-4-yl}-sulfamide or of a solvate of that compound, characterized by:
form A of the COMPOUND comprising the presence of peaks in the X-ray powder diffraction diagram at the following angles of refraction 2θ: 17.8°, 20.0°, and 23.5°; or
form C of the COMPOUND comprising the presence of peaks in the X-ray powder diffraction diagram at the following angles of refraction 2θ: 9.7°, 15.7°, and 22.0°; or
form D of the COMPOUND comprising the presence of peaks in the X-ray powder diffraction diagram at the following angles of refraction 2θ: 4.6°, 16.8°, and 20.1°; or
form E of an acetonitrile solvate of the COMPOUND comprising the presence of peaks in the X-ray powder diffraction diagram at the following angles of refraction 2θ: 9.5°, 16.5°, and 18.2°; or
form J of the COMPOUND comprising the presence of peaks in the X-ray powder diffraction diagram at the following angles of refraction 2θ: 4.0°, 16.1°, and 21.9°; or
form K of a dimethylsulfoxide solvate of the COMPOUND comprising the presence of peaks in the X-ray powder diffraction diagram at the following angles of refraction 2θ: 16.9°, 19.3°, and 24.8°; or
form L of an ethanol solvate of the COMPOUND comprising the presence of peaks in the X-ray powder diffraction diagram at the following angles of refraction 2θ: 11.3°, 16.4°, and 20.3°;
wherein said X-ray powder diffraction diagram is obtained by using combined Cu Kα1 and Kα2 radiation, without Kα2 stripping; and the accuracy of the 2θ values is in the range of 2θ+/−0.20.

It is understood, that the crystalline forms according to embodiment 1) comprise the COMPOUND in a crystalline form of the free base (i.e. not in form of a salt). Furthermore, said crystalline forms may comprise non-coordinated and/or coordinated solvent. Coordinated solvent is used herein as term for a crystalline solvate. Likewise, non-coordinated solvent is used herein as term for physiosorbed or physically entrapped solvent (definitions according to Polymorphism in the Pharmaceutical Industry (Ed. R. Hilfiker, V C H, 2006), Chapter 8: U. J. Griesser: The Importance of Solvates). Crystalline forms A and C are anhydrate or ansolvate forms i.e. they comprise no coordinated water, but may comprise non-coordinated solvent such as isopropanol, methanol, ethanol and/or water, crystalline form B is a DCM solvate, crystalline form E is a MeCN solvate, crystalline form K is a DMSO solvate, and crystalline form L is an ethanol solvate.

It is to be understood that the present invention covers each of the forms A, C, D, E, J, K and L individually, as well as two, three, four, five, six or seven individual forms. Preferred are forms A and/or C, especially form A.

2) Another embodiment relates to a crystalline form of the COMPOUND or of a solvate of that compound, characterized by
form A of the COMPOUND comprising the presence of peaks in the X-ray powder diffraction diagram at the following angles of refraction 2θ: 17.8°, 18.6°, 20.0°, 23.2° and 23.5°; or
form C of the COMPOUND comprising the presence of peaks in the X-ray powder diffraction diagram at the following angles of refraction 2θ: 7.8°, 9.7°, 15.7°, 19.8° and 22.0°; or
form D of the COMPOUND comprising the presence of peaks in the X-ray powder diffraction diagram at the following angles of refraction 2θ: 4.6°, 16.8°, 19.6°, 20.1° and 20.6°; or
form E of an acetonitrile solvate of the COMPOUND comprising the presence of peaks in the X-ray powder diffraction diagram at the following angles of refraction 2θ: 9.5°, 15.6°, 16.5°, 18.2° and 26.6°; or
form J of the COMPOUND comprising the presence of peaks in the X-ray powder diffraction diagram at the following angles of refraction 2θ: 4.0°, 16.1°, 19.0°, 20.7° and 21.9°; or
form K of a dimethylsulfoxide solvate of the COMPOUND comprising the presence of peaks in the X-ray powder diffraction diagram at the following angles of refraction 2θ: 16.9°, 19.3°, 20.8°, 21.2° and 24.8°; or
form L of an ethanol solvate of the COMPOUND comprising the presence of peaks in the X-ray powder diffraction diagram at the following angles of refraction 2θ: 9.3°, 11.30, 16.40, 20.0° and 20.30;
wherein said X-ray powder diffraction diagram is obtained by using combined Cu Kα1 and Kα2 radiation, without Kα2 stripping; and the accuracy of the 2θ values is in the range of 2θ+/−0.2°. Preferred are forms A and/or C, especially form A.

3) Another embodiment relates to a crystalline form of the COMPOUND or of a solvate of that compound, characterized by:
form A of the COMPOUND comprising the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; or
form C of the COMPOUND comprising the presence of peaks in the X-ray powder diffraction diagram at the following angles of refraction 2θ: 7.8°, 9.7°, 15.7°, 17.2°, 17.8°, 18.8°, 19.8°, 22.0°, 23.6°, and 25.3°; or
form D of the COMPOUND comprising the presence of peaks in the X-ray powder diffraction diagram at the following angles of refraction 2θ: 4.6°, 16.4°, 16.8°, 19.3°, 19.6°, 20.1°, 20.6°, 23.0°, 23.5°, and 25.1°; or
form E of an acetonitrile solvate of the COMPOUND comprising the presence of peaks in the X-ray powder diffraction diagram at the following angles of refraction 2θ: 9.5°, 15.6°, 16.0°, 16.5°, 18.2°, 18.7°, 25.3°, 26.6°, 29.6°, and 30.2°; or
form J of the COMPOUND comprising the presence of peaks in the X-ray powder diffraction diagram at the following angles of refraction 2θ: 4.0°, 6.5°, 9.0°, 16.1°, 19.0°, 19.8°, 20.7°, 21.9°, 24.1°, and 24.8°; or
form K of a dimethylsulfoxide solvate of the COMPOUND comprising the presence of peaks in the X-ray powder diffraction diagram at the following angles of refraction 2θ: 10.9°, 13.70, 16.9°, 18.2°, 19.3°, 20.8°, 21.2°, 24.3°, 24.8°, and 26.70; or
form L of an ethanol solvate of the COMPOUND comprising the presence of peaks in the X-ray powder diffraction diagram at the following angles of refraction 2θ: 9.1°, 9.3°, 11.3°, 14.8°, 16.4°, 20.0°, 20.3°, 22.8°, 24.5°, and 24.7°;
wherein said X-ray powder diffraction diagram is obtained by using combined Cu Kα1 and Kα2 radiation, without Kα2 stripping; and the accuracy of the 2θ values is in the range of 2θ+/−0.2°. Preferred are forms A and/or C, especially form A.

4) Another embodiment relates to a crystalline form of the COMPOUND or of a solvate thereof, characterized by:

form A of the COMPOUND comprising the presence of peaks in the X-ray powder diffraction diagram at the following angles of refraction 2θ: 9.8°, 9.9°, 11.7°, 14.5°, 15.4°, 15.6°, 16.9°, 17.2°, 17.8°, 18.6°, 19.9°, 20.0°, 21.5°, 21.9°, 22.8°, 23.2°, 23.5°, 24.9°, 25.1°, 25.3°, 25.6°, 25.9°, 27.1°, 27.3°, 28.5°, 29.0°, 29.4°, 30.1° and 30.60; or form C of the COMPOUND comprising the presence of peaks in the X-ray powder diffraction diagram at the following angles of refraction 2θ: 7.8°, 9.7°, 15.7°, 17.2°, 17.8°, 18.8°, 19.8°, 20.1°, 20.6°, 21.6°, 22.0°, 23.4°, 23.6°, 24.1°, 24.5°, 25.1°, 25.3°, 25.7°, 26.8°, 27.1°, 28.5°, 30.8° and 30.8°; or form D of the COMPOUND comprising the presence of peaks in the X-ray powder diffraction diagram at the following angles of refraction 2θ: 4.6°, 8.4°, 8.6°, 16.4°, 16.8°, 17.2°, 18.6°, 18.9°, 19.3°, 19.6°, 20.1°, 20.6°, 20.8°, 22.0°, 22.7°, 23.0°, 23.5°, 23.8°, 24.2°, 24.7°, 25.1°, 25.4°, 25.6°, 26.2°, 26.8°, 27.2°, 28.1° and 28.1°; or form E of an acetonitrile solvate of the COMPOUND comprising the presence of peaks in the X-ray powder diffraction diagram at the following angles of refraction 2θ: 9.0°, 9.5°, 11.3°, 14.5°, 14.8°, 15.6°, 16.0°, 16.5°, 18.2°, 18.7°, 18.9°, 20.2°, 20.7°, 22.8°, 23.9°, 24.5°, 25.3°, 25.6°, 26.0°, 26.6°, 27.5°, 29.6°, 30.2° and 33.0°; or form J of the COMPOUND comprising the presence of peaks in the X-ray powder diffraction diagram at the following angles of refraction 2θ: 4.0°, 4.8°, 6.5°, 9.0°, 16.1°, 17.2°, 18.7°, 19.0°, 19.4°, 19.8°, 20.7°, 21.2°, 21.9°, 22.6°, 23.2°, 24.1°, 24.8°, 25.6°, 27.0°, 28.2°, 29.0°, 30.4° and 30.8°; or form K of a dimethylsulfoxide solvate of the COMPOUND comprising the presence of peaks in the X-ray powder diffraction diagram at the following angles of refraction 2θ: 10.9°, 16.9°, 18.2°, 18.4°, 18.6°, 18.7°, 19.3°, 20.8°, 21.2°, 21.9°, 24.3°, 24.8°, 25.4°, 25.8°. 26.7°. 27.7°. 27.8°. 28.6°. 29.4°. 31.5° and 31.8°; or form L of an ethanol solvate of the COMPOUND comprising the presence of peaks in the X-ray powder diffraction diagram at the following angles of refraction 2θ: 9.1°, 9.3°, 11.3°, 12.2°, 14.6°, 14.8°, 15.7°, 16.1°, 16.4°, 17.9°, 18.2°, 18.7°, 20.0°, 20.3°, 22.6°, 22.8°, 23.2°, 24.1°, 24.5°, 24.7°, 25.5°, 25.9°, 26.4°, 26.8°, 27.7°, 28.2°, 29.7°, 29.5°, 29.8°, 30.3°, 30.5° and 32.4°;

wherein said X-ray powder diffraction diagram is obtained by using combined Cu Kα1 and Kα2 radiation, without Kα2 stripping; and the accuracy of the 2θ values is in the range of 2θ+/−0.2°. Preferred are forms A and/or C, especially form A.

5) Another embodiment relates to a crystalline form of the COMPOUND or of a solvate thereof; characterized by:

form A of the COMPOUND comprising the presence of peaks in the X-ray powder diffraction diagram at the following angles of refraction 2θ: 9.8° (18%), 9.9° (18%), 11.7° (14%), 14.5° (10%), 15.4° (14%), 15.6° (29%), 16.9° (19%), 17.2° (16%), 17.80 (100%), 18.6° (50%), 19.9° (54%), 20.0° (67%), 21.5° (24%), 21.9° (10%), 22.8° (18%), 23.2° (49%), 23.5° (83%), 24.9° (32%), 25.1° (20%), 25.3° (24%), 25.6° (33%), 25.9° (16%), 27.1° (23%), 27.3° (39%), 28.5° (13%), 29.0° (23%), 29.40 (15%), 30.1° (12%) and 30.6° (10%); or form C of the COMPOUND comprising the presence of peaks in the X-ray powder diffraction diagram at the following angles of refraction 2θ: 7.8° (23%), 9.7° (42%), 15.7° (37%), 17.2° (16%), 17.8° (15%), 18.8° (26%), 19.8° (71%), 20.1° (51%), 20.6° (15%), 21.6° (15%), 22.0° (100%), 23.4° (27%), 23.6° (40%), 24.1° (23%), 24.5° (16%), 25.1° (13%), 25.3° (39%), 25.7° (28%), 26.8° (19%), 27.1° (16%), 28.50 (31%), 30.8° (13%) and 30.8° (13%); or form D of the COMPOUND comprising the presence of peaks in the X-ray powder diffraction diagram at the following angles of refraction 2θ: 4.6° (27%), 8.4° (15%), 8.6° (11%), 16.4° (17%), 16.8° (26%), 17.2° (10%), 18.6° (11%), 18.9° (18%), 19.30 (40%), 19.6° (45%), 20.1°(100%), 20.6° (55%), 20.8° (26%), 22.0° (10%), 22.70 (14%), 23.0° (24%), 23.5° (32%), 23.8° (12%), 24.2° (17%), 24.7° (20%), 25.10 (55%), 25.4° (22%), 25.6° (14%), 26.2° (16%), 26.8° (17%), 27.2° (28%), 28.1° (21%) and 28.1° (19%); or form E of an acetonitrile solvate of the COMPOUND comprising the presence of peaks in the X-ray powder diffraction diagram at the following angles of refraction 2θ: 9.0° (21%), 9.5° (56%), 11.3° (61%), 14.5° (41%), 14.8° (15%), 15.6° (47%), 16.0° (26%), 16.5° (100%), 18.2° (84%), 18.7° (73%), 18.9° (56%), 20.2° (20%), 20.7° (56%), 22.80 (96%), 23.9° (22%), 24.5° (70%), 25.3° (77%), 25.6° (29%), 26.0° (14%), 26.60 (66%), 27.50 (27%), 29.60 (31%), 30.2° (66%) and 33.0° (13%); or form J of the COMPOUND comprising the presence of peaks in the X-ray powder diffraction diagram at the following angles of refraction 2θ: 4.0° (44%), 4.8° (14%), 6.5° (23%), 9.0° (27%), 16.1° (40%), 17.2° (11%), 18.7° (22%), 19.0° (58%), 19.40 (28%), 19.8° (46%), 20.7° (57%), 21.2° (17%), 21.9° (100%), 22.6° (14%), 23.20 (23%), 24.1° (37%), 24.8° (40%), 25.6° (42%), 27.0° (29%), 28.2° (27%), 29.0° (20%), 30.4° and 30.8° (10%); or form K of a dimethylsulfoxide solvate of the COMPOUND comprising the presence of peaks in the X-ray powder diffraction diagram at the following angles of refraction 2θ: 10.9° (16%), 16.9° (18%), 18.2° (26%), 18.4° (30%), 18.6° (29%), 18.7° (55%), 19.30 (100%), 20.8° (35%), 21.2° (47%), 21.9° (26%), 24.3° (21%), 24.8° (24%), 25.4° (29%), 25.8° (22%), 26.7° (34%), 27.7° (13%), 27.8° (14%), 28.6° (15%), 29.40 (18%), 31.5° (23%) and 31.8° (12%); or form L of an ethanol solvate of the COMPOUND comprising the presence of peaks in the X-ray powder diffraction diagram at the following angles of refraction 2θ: 9.10 (31%), 9.3° (34%), 11.3° (49%), 12.2° (10%), 14.6° (17%), 14.8° (46%), 15.7° (16%), 16.1° (10%), 16.4° (80%), 17.9° (17%), 18.2° (19%), 18.7° (96%), 20.0° (38%), 20.30 (100%), 22.6° (11%), 22.8° (76%), 23.2° (50%), 24.1° (14%), 24.5° (56%), 24.70 (68%), 25.5° (46%), 25.9° (32%), 26.4° (14%), 26.8° (22%), 27.7° (38%), 28.20 (12%), 29.7° (11%), 29.5° (64%), 29.8° (14%), 30.3° (14%), 30.5° (13%) and 32.4° (16%);

wherein said X-ray powder diffraction diagram is obtained by using combined Cu Kul and Kα2 radiation, without Kα2 stripping; and the accuracy of the 2θ values is in the range of 2θ+/−0.2°. Preferred are forms A and C, especially form A.

The present data show peaks having a relative intensity, as compared to the most intense peak in the diagram, of the following percentages (relative peak intensitites given in parentheses) at the indicated angles of refraction 2theta (selected peaks from the range 3-33° 2theta with relative intensity larger then 10% are reported).

6) Another embodiment relates to a crystalline form of the COMPOUND or of a solvate thereof which essentially shows the X-ray powder diffraction pattern as depicted in any one of the FIGS. 1, 3, 4, 5, 6, 7 and 8, wherein said X-ray powder diffraction diagram is obtained by using combined Cu Kα1 and Kα2 radiation, without Kα2 stripping; and the accuracy of the 2θ values is in the range of 2θ+/−0.2°.

In this context the term "essentially" means that at least the major peaks of the diagram depicted in said figures, i.e. those having a relative intensity of more than 10%, especially more than 20%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

7) A particular sub-embodiment of embodiment 6) relates to a crystalline form of COMPOUND which essentially shows the X-ray powder diffraction pattern as depicted in FIG. 1, wherein said X-ray powder diffraction diagram is obtained by using combined Cu Kα1 and Kα2 radiation, without Kα2 stripping; and the accuracy of the 2θ values is in the range of 2θ+/−0.2°.

8) In another embodiment the present invention relates to a crystalline form of the COMPOUND or of a solvate thereof wherein
  (a) form A is obtainable by crystallisation of the COMPOUND in an aqueous solution at pH 6.2 to 6.8;
  (b) form B is obtainable by crystallisation of the COMPOUND from DCM at pH 7;
  (c) form C is obtainable by crystallisation of the COMPOUND from MeOH, EtOH or propan-2-ol;
  (d) form D is obtainable by crystallisation of form A from methyl-ethylketone;
  (e) form E is obtainable by crystallisation of form A from MeCN;
  (j) form J is obtainable by crystallisation of form B from DMSO and water;
  (k) form K is obtainable by crystallisation of the COMPOUND in an aqueous solution;
  (l) form L is obtainable by crystallisation of form K from EtOH.

9) Another embodiment of the present invention relates to a crystalline form A of the COMPOUND comprising the presence of peaks in the X-ray powder diffraction diagram at the following angles of refraction 2θ: 17.8°, 20.0°, and 23.5°; whereby it is an anhydrate or ansolvate form. It is understood that the X-ray powder diffraction diagram may further comprise the peaks as disclosed in embodiment 2), 3), 4), 5) or 6). It is further understood that said crystalline form may be further characterized by an endothermic event with a peak of the endotherm observed at about 159° C. as determined by DSC, e.g. using the method disclosed in the experimental part.

10) Another embodiment of the present invention relates to a crystalline form A of the COMPOUND comprising the presence of peaks in the X-ray powder diffraction diagram at the following angles of refraction 2θ: 17.8°, 20.0°, and 23.5°; whereby it is an anhydrate or ansolvate form which is obtainable by crystallisation in an aqueous solution at pH 6.2 to 6.8. It is understood that the X-ray powder diffraction diagram may further comprise the peaks as disclosed in embodiment 2), 3), 4), 5) or 6).

11) Another embodiment of the present invention relates to a crystalline form B of a dichloromethane solvate of the COMPOUND comprising the presence of peaks in the X-ray powder diffraction diagram at the following angles of refraction 2θ: 16.2°, 18.6°, and 20.3° (notably 16.2°, 18.6°, 20.3°, 22.4° and 24.3°, especially 9.0°, 11.2°, 16.2°, 18.0°, 18.6°, 19.8°, 20.3°, 22.4°, 22.9° and 24.3°).

12) Another embodiment of the present invention relates to a crystalline form B of a dichloromethane solvate of the COMPOUND comprising the presence of peaks in the X-ray powder diffraction diagram at the following angles of refraction 2θ: 16.2°, 18.6°, and 20.3° (notably 16.2°, 18.6°, 20.3°, 22.4° and 24.3°, especially 9.0°, 11.2°, 16.2°, 18.0°, 18.6°, 19.8°, 20.3°, 22.4°, 22.9° and 24.3°); whereby this form is obtainable by crystallisation from dichloromethane at pH 7.

13) Another embodiment of the present invention relates to a crystalline form C of the COMPOUND comprising the presence of peaks in the X-ray powder diffraction diagram at the following angles of refraction 2θ: 9.7°, 15.7°, and 22.0°; whereby it is an anhydrate or ansolvate form. It is understood that the X-ray powder diffraction diagram may further comprise the peaks as disclosed in embodiment 2), 3), 4), 5) or 6). It is further understood that said crystalline form may be further characterized by an endothermic event with a peak of the endotherm observed at about 153° C. as determined by DSC, e.g. using the method disclosed in the experimental part.

14) Another embodiment of the present invention relates to a crystalline form C of the COMPOUND comprising the presence of peaks in the X-ray powder diffraction diagram at the following angles of refraction 2θ: 9.7°, 15.7°, and 22.0°; whereby it is an anhydrate or ansolvate form which is obtainable by crystallisation MeOH, EtOH or propan-2-ol. It is understood that the X-ray powder diffraction diagram may further comprise the peaks as disclosed in embodiment 2), 3), 4), 5) or 6).

15) Another embodiment of the present invention relates to a crystalline form D of the COMPOUND comprising the presence of peaks in the X-ray powder diffraction diagram at the following angles of refraction 2θ: 4.6°, 16.8°, and 20.1°; whereby it is obtainable by crystallisation of form A from methyl-ethylketone. It is understood that the X-ray powder diffraction diagram may further comprise the peaks as disclosed in embodiment 2), 3), 4), 5) or 6).

16) Another embodiment of the present invention relates to a crystalline form E of an acetonitrile solvate of the COMPOUND comprising the presence of peaks in the X-ray powder diffraction diagram at the following angles of refraction 2θ: 9.5°, 16.5°, and 18.2°. It is understood that the X-ray powder diffraction diagram may further comprise the peaks as disclosed in embodiment 2), 3), 4), 5) or 6).

17) Another embodiment of the present invention relates to a crystalline form E of an acetonitrile solvate of the COMPOUND comprising the presence of peaks in the X-ray powder diffraction diagram at the following angles of refraction 2θ: 9.5°, 16.5°, and 18.2°; whereby this form is obtainable by crystallisation of form A from acetonitrile. It is understood that the X-ray powder diffraction diagram may further comprise the peaks as disclosed in embodiment 2), 3), 4), 5) or 6).

18) Another embodiment of the present invention relates to a crystalline form J of the COMPOUND comprising the presence of peaks in the X-ray powder diffraction diagram at the following angles of refraction 2θ: 4.0°, 16.1°, and 21.9°; whereby it is obtainable by crystallisation of form B of a dichloromethane solvate of the COMPOUND from DMSO and water. It is understood that the X-ray powder diffraction diagram may further comprise the peaks as disclosed in embodiment 2), 3), 4), 5) or 6).

19) Another embodiment of the present invention relates to a crystalline form K of a dimethylsulfoxide solvate of the COMPOUND comprising the presence of peaks in the X-ray powder diffraction diagram at the following angles of refraction 2θ: 16.9°, 19.3°, and 24.8°. It is understood that the X-ray powder diffraction diagram may further comprise the peaks as disclosed in embodiment 2), 3), 4), 5) or 6).

20) Another embodiment of the present invention relates to a crystalline form K of a dimethylsulfoxide solvate of the COMPOUND comprising the presence of peaks in the X-ray powder diffraction diagram at the following angles of refraction 2θ: 16.9°, 19.3°, and 24.8°; whereby this form is obtainable by crystallisation in an aqueous solution. It is understood that the X-ray powder diffraction diagram may further comprise the peaks as disclosed in embodiment 2), 3), 4), 5) or 6).

21) Another embodiment of the present invention relates to a crystalline form L of an ethanol solvate of the COMPOUND comprising the presence of peaks in the X-ray powder diffraction diagram at the following angles of refraction 2θ: 11.3°, 16.4°, and 20.3°; whereby it is obtainable by crystallisation of form K from ethanol. It is understood that the X-ray powder diffraction diagram may further comprise the peaks as disclosed in embodiment 2), 3), 4), 5) or 6).

For avoidance of any doubt, whenever one of the above embodiments refers to "peaks in the X-ray powder diffraction diagram at the following angles of refraction 2θ", said X-ray powder diffraction diagram is obtained by using combined Cu Kα1 and Kα2 radiation, without Kα2 stripping; and it should be understood that the accuracy of the 2 θ values as provided herein is in the range of +/−0.1-0.2°. Notably, when specifying an angle of refraction 2theta (2 θ) for a peak in the invention embodiments and the claims, the 2 θ value given is to be understood as an interval from said value minus 0.2° to said value plus 0.2° (2 θ+/−0.2°); and preferably from said value minus 0.1° to said value plus 0.1° (2 θ+/−0.1°).

When defining the presence of peak in e.g. an X-ray powder diffraction diagram, a common approach is to do this in terms of diagram depicted (S=signal, N=noise). According to this definition, when stating that a peak has to be present in an X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., preferably to an interval extending from Y minus 5° C. to Y plus 5° C., notably to an interval extending from Y minus 3° C. to Y plus 3° C. Room temperature means a temperature of about 25° C. When in the current application the term n equivalent(s) is used wherein n is a number, it is meant and within the scope of the current application that n is referring to about the number n, preferably n is referring to the exact number n.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

22) Another embodiment of the present invention relates to an amorphous form of the COMPOUND {5-(4-bromophenyl)-6-[2-(5-bromo-pyrimidin-2-yloxy)-ethoxy]-pyrimidin-4-yl}-sulfamide. Thus, the amorphous form may be obtained by milling form A. For Example, the amorphous form is obtainable by milling in a ball mill (MM200 Retsch Ball Mill, 2 agate beads), 30 min at 30 Hz at ambient temperature.

23) The crystalline forms, especially the essentially pure crystalline forms, of the COMPOUND according to any one of embodiments 1) to 21) can be used as medicaments, e.g. in the form of pharmaceutical compositions for enteral or parenteral administration.

The term "essentially pure" is understood in the context of the present invention to mean especially that at least 90, preferably at least 95, and most preferably at least 99 percent by weight of COMPUND is present in the respective crystalline form.

24) Another embodiment thus relates to a crystalline form of COMPOUND according to any one of embodiments 1) to 21) for use as a medicament.

The crystalline solid, especially the essentially pure crystalline solid, of COMPOUND according to any one of embodiments 1) to 21) may be used as single component or as mixtures with other crystalline forms or the amorphous form of COMPOUND.

The production of the pharmaceutical compositions can be effected in a manner which will be familiar to any person skilled in the art (see for example Remington, The Science and Practice of Pharmacy, 21st Edition (2005), Part 5, "Pharmaceutical Manufacturing" [published by Lippincott Williams & Wilkins]) by bringing the crystalline forms of the present invention, optionally in combination with other therapeutically valuable substances, into a galenical administration form together with suitable, non-toxic, inert, pharmaceutically acceptable solid or liquid carrier materials and, if desired, usual pharmaceutical adjuvants.

25) Another embodiment of the present invention relates to a crystalline form of the COMPOUND or of a solvate of that compound, according to any one of embodiments 1) to 21), for the use in the manufacture of a pharmaceutical composition, wherein said pharmaceutical composition comprises as active ingredient the compound {5-(4-bromophenyl)-6-[2-(5-bromo-pyrimidin-2-yloxy)-ethoxy]-pyrimidin-4-yl}-sulfamide, and at least one therapeutically inert excipient.

Such pharmaceutical compositions according to embodiment 25) are especially useful for the treatment of hypertension, pulmonary hypertension, coronary diseases, cardiac insufficiency, renal and myocardial ischemia, renal failure, cerebral ischemia, dementia, migraine, subarachnoidal hemorrhage, Raynaud's syndrome, digital ulcers or portal hypertension as well as for the treatment or prevention of atherosclerosis, restenosis after balloon or stent angioplasty, inflammation, stomach and duodenal ulcer, cancer, melanoma, prostate cancer, prostatic hypertrophy, erectile dysfunction, hearing loss, amaurosis, chronic bronchitis, asthma, pulmonary fibrosis, gram negative septicemia, shock, sickle cell anemia, glomerulonephritis, renal colic, glaucoma, connective tissue diseases, diabetic complications, complications of vascular or cardiac surgery or after organ transplantation, complications of cyclosporin treatment, pain or hyperlipidemia. The pharmaceutical compositions according to embodiment 25) are also useful for the treatment of Chronic Kidney Disease (CKD), especially CKD of stages 1 to 4 as defined by the Kidney Disease Improving Global Outcomes (KDIGO) Guidelines (and notably CKD of stage 3), and in particular CKD (notably of these stages) caused by essential hypertension.

Preferably, they are useful for in the treatment of a disease selected from the group consisting of hypertension, pulmonary hypertension, diabetic arteriopathy, heart failure, erectile dysfunction, angina pectoris and CKD [especially CKD of stages 1 to 4 as defined by the Kidney Disease Improving Global Outcomes (KDIGO) Guidelines (and notably CKD of stage 3); and in particular CKD (notably of these stages) caused by essential hypertension].

Moreover, they are useful in the treatment of a disease selected from the group consisting of essential hypertension, resistant hypertension, pulmonary hypertension and pulmonary arterial hypertension (and notably in the treatment of resistant hypertension).

Essential hypertension (also called primary hypertension or idiopathic hypertension) is the form of hypertension that by definition has no identifiable cause. It represents a significant global public health concern, contributing to vascular and renal morbidity and to cardiovascular mortality. The diagnosis of essential hypertension is made when the average of multiple systolic blood pressure measurements on 2 or more subsequent visits is consistently equal to or above a certain threshold value $T_{SBP}$. Individuals with high normal blood pressure tend to maintain pressures that are above average for the general population and are at greater risk for development of definite hypertension and cardiovascular events than the general population. The threshold value $T_{SBP}$ above which treatment is recommended is regularly discussed among clinicians (see e.g. Mancia et al, *J. Hypertens.* (2013), 31, 1281-1357); accordingly, depending on the patient's general condition and age, $T_{SBP}$ could be 140 or 130 mm Hg, or another suitable value.

The term "resistant hypertension" in the present invention is defined as blood pressure that remains above goal in spite of the concurrent use of 3 antihypertensive agents of different classes. One of the 3 agents should be a diuretic and all agents should be prescribed at optimal/maximal dose amounts. As defined, resistant hypertension patients include patients whose blood pressure is controlled with use of more than 3 medications. That is, patients whose blood pressure is controlled but require 4 or more medications to do so should be considered resistant to treatment (see e.g. Mancia et al, *J. Hypertens.* (2013), 31, 1281-1357).

"Diuretic" in particular means in the present application a diuretic of the thiazide class (a thiazide-like diuretic) such as especially chlorthalidone, hydrochlorothiazide, chlorthiazide, indapamide, or metolazone. Preferred diuretics are chlorthalidone or hydrochlorothiazide.

The invention, thus, further relates to COMPOUND, especially a crystalline form of COMPOUND according to any one of embodiments 1) to 21) (in particular crystalline Form A or C), wherein COMPOUND/said crystalline form is used as a medicament, especially for the treatment of resistant hypertension; wherein COMPOUND/said crystalline form is used alone or (preferably) in combination (preferably for simultaneously adminiatration, including a fixed dose combination) with a diuretic, in particular hydrochlorothiazide (HCTZ or HCT). In a sub-embodiment, said combination of COMPOUND/said crystalline form according to any one of embodiments 1) to 21) (in particular crystalline Form A or C) with a diuretic, in particular hydrochlorothiazide (HCTZ or HCT) for the treatment of resistant hypertension; may require further combination (preferably for simultaneously adminiatration, including a fixed dose combination) with one or two additional active ingredients that are antihypertensive agents of different classes (especially a CCB and/or an ARB), in particular valsartan. The invention, thus, especially relates to pharmaceutical compositions comprising COMPOUND/the respective crystalline form of COMPOUND as defined in any one of embodiments 26) to 31) below; comprising as active ingredients, in addition to COMPOUND/the respective crystalline form of COMPOUND, a diuretic, in particular hydrochlorothiazide (HCTZ or HCT); and optionally further comprising one or two active ingredients that are antihypertensive agents of different classes (especially a CCB and/or an ARB); in particular further comprising valsartan.

26) Another embodiment of the present invention relates to a pharmaceutical composition comprising as active ingredient a crystalline form of the COMPOUND according to any one of embodiments 1) to 21), and at least one therapeutically inert excipient.

27) The invention thus also relates to a solid pharmaceutical composition (in particular in the form of a tablet) comprising COMPOUND, especially a crystalline form of the COMPOUND according to any one of embodiments 1) to 21) (especially solid form A of the COMPOUND, as described in any one of embodiments 1) to 7)), microcrystalline cellulose, lactose, hydroxypropylcellulose, croscarmellose sodium and magnesium stearate; it will in particular relate to a solid pharmaceutical composition (in particular in the form of a tablet) consisting of a crystalline form of the COMPOUND according to any one of embodiments 1) to 21) (especially solid form A thereof, as described in any one of embodiments 1) to 7)), microcrystalline cellulose, lactose, hydroxypropylcellulose, croscarmellose sodium and magnesium stearate.

28) Preferably, the solid pharmaceutical composition of embodiment 27) will comprise COMPOUND, especially the crystalline form of the COMPOUND according to any one of embodiments 1) to 21) (especially solid form A of the COMPOUND, as described in any one of embodiments 1) to 7)) in a total amount from 1 to 25% (especially 5 to 25%) in weight based on the total weight of the pharmaceutical composition, microcrystalline cellulose in a total amount from 20 to 35% (especially 20 to 30%) in weight based on the total weight of the pharmaceutical composition, lactose in a total amount from 40 to 65% in weight based on the total weight of the pharmaceutical composition, hydroxypropylcellulose in a total amount from 1 to 3% in weight based on the total weight of the pharmaceutical composition, croscarmellose sodium in a total amount from 2 to 8% in weight based on the total weight of the pharmaceutical composition and magnesium stearate in a total amount from 0.2 to 2% in weight based on the total weight of the pharmaceutical composition, whereby the total percent in weight of the solid pharmaceutical composition will always be 100; the aforementioned solid pharmaceutical composition will particularly be in the form of a tablet.

Such pharmaceutical compositions according to any of embodiments 26) to 28) are especially useful for the treatment of endothelin related diseases and disorders, notably the diseases and disorders of embodiment 25).

29) A further embodiment of the invention relates to a pharmaceutical composition according to any one of embodiments 26) to 28), wherein said pharmaceutical composition is in form of a tablet.

30) In particular, the pharmaceutical composition of embodiment 29) will be in the form of a tablet consisting of the solid form A of the COMPOUND (as described in any one of embodiments 1) to 7)) in a total amount from 1 to 25% (especially 5 to 25%) in weight based on the total weight of the pharmaceutical composition, microcrystalline cellulose in a total amount from 20 to 35% (especially 20 to 30%) in weight based on the total weight of the pharmaceutical composition, lactose in a total amount from 40 to 65% in weight based on the total weight of the pharmaceutical composition, hydroxypropylcellulose in a total amount from 1 to 3% in weight based on the total weight of the pharmaceutical composition, croscarmellose sodium in a total amount from 2 to 8% in weight based on the total weight of the pharmaceutical composition and magnesium stearate in a total amount from 0.2 to 2% in weight based on the total weight of the pharmaceutical composition, whereby the total percent in weight of the solid pharmaceutical composition will always be 100.

A tablet according to embodiment 29) or 30) can optionally be coated with a suitable protective pellicle. Said protective pellicle will notably prevent direct contact of the pharmaceutical composition with moisture; it may also ease imprints that may be desired to be used in order to distinguish the pharmaceutical composition from others.

The coating material for making such protective pellicle may include a low water vapour permeability polymer (such as a polyvinyl alcohol (e.g. Aquapolish® white PVA from manufacturer Biogrund) or dimethylaminoethyl methacrylate (e.g. EUDRAGIT© E PO)). The coating material can further include a plasticizing agent (e.g. propylene glycol, triacetyne, dibutyl phthalate or dibutyl sebacate), a surfactant (e.g. sodium lauryl sulphate or a polysorbate such as Tween®) and/or a lubricant/glidant (e.g. stearic acid, magnesium or calcium stearate or talc). Moreover, the coating material can also include a pigment (e.g. iron (II) oxide, iron(III) oxide or titanium oxide) to give the tablet a coloured aspect.

31) A further embodiment of the invention relates to a pharmaceutical composition according to any one of embodiments 26) to 28), wherein said pharmaceutical composition is in form of a capsule.

For avoidance of any doubt, embodiments 25), 26), 27), 28), 29), 30) or 31) especially refer to the crystalline forms according to any one of embodiments 1) to 21) which is suitable/which is used as final isolation step of COMPOUND (e.g. in order to meet the purity requirements of pharmaceutical production), whereas the final pharmaceutical composition according to embodiment 25), 26), 27), 28), 29), 30) or 31) may or may not contain said crystalline form (e.g. because the originally crystalline form of COMPOUND is further transformed during the manufacturing process and/or is dissolved in the pharmaceutically acceptable carrier material(s); thus, in the final pharmaceutical composition, COMPOUND may be present in non-crystalline form, in another crystalline form, or in dissolved form, or the like).

32) A further embodiment of the invention relates to COMPOUND or a pharmaceutically acceptable salt thereof, especially a crystalline form of COMPOUND according to any one of embodiments 1) to 21), for use in the treatment of hypertension, pulmonary hypertension, coronary diseases, cardiac insufficiency, renal and myocardial ischemia, renal failure, cerebral ischemia, dementia, migraine, subarachnoidal hemorrhage, Raynaud's syndrome, digital ulcers or portal hypertension as well as for the treatment or prevention of atherosclerosis, restenosis after balloon or stent angioplasty, inflammation, stomach and duodenal ulcer, cancer, melanoma, prostate cancer, prostatic hypertrophy, erectile dysfunction, hearing loss, amaurosis, chronic bronchitis, asthma, pulmonary fibrosis, gram negative septicemia, shock, sickle cell anemia, glomerulonephritis, renal colic, glaucoma, connective tissue diseases, diabetic complications, complications of vascular or cardiac surgery or after organ transplantation, complications of cyclosporin treatment, pain, hyperlipidemia or CKD [especially CKD of stages 1 to 4 as defined by the Kidney Disease Improving Global Outcomes (KDTGO) Guidelines (and notably CKD of stage 3), and in particular CKD (notably of these stages) caused by essential hypertension].

33) A further embodiment of the invention relates to COMPOUND or a pharmaceutically acceptable salt thereof, especially a crystalline form of COMPOUND according to any one of embodiments 1) to 21), for use in the treatment of a disease selected from the group consisting of hypertension, pulmonary hypertension, diabetic arteriopathy, heart failure, erectile dysfunction, angina pectoris and CKD [especially CKD of stages 1 to 4 as defined by the Kidney Disease Improving Global Outcomes (KDIGO) Guidelines (and notably CKD of stage 3), and in particular CKD (notably of these stages) caused by essential hypertension].

34) A further embodiment of the invention relates to COMPOUND or a pharmaceutically acceptable salt thereof, especially a crystalline form of COMPOUND according to any one of embodiments 1) to 21), for use in the treatment of a disease selected from the group consisting of essential hypertension, resistant hypertension, pulmonary hypertension and pulmonary arterial hypertension (and notably for use in the treatment of resistant hypertension).

For avoidance of any doubt, if a certain crystalline form of COMPOUND is described as useful for the prevention/prophylaxis or treatment of certain diseases, such compounds are likewise suitable for use in the preparation of a medicament for the prevention/prophylaxis or treatment of said diseases. Likewise, such compounds are also suitable in a method for the prevention/prophylaxis or treatment of such diseases, comprising administering to a subject (mammal, especially human) in need thereof, an effective amount of such compound.

35) A further embodiment of the invention relates to the use of COMPOUND or a pharmaceutically acceptable salt thereof, especially of a crystalline form of COMPOUND according to any one of embodiments 1) to 21), for the preparation of a medicament intended for the treatment of any one of the diseases or disorders mentioned in embodiment 32).

36) A further embodiment of the invention relates to the use of COMPOUND or a pharmaceutically acceptable salt thereof, especially of a crystalline form of COMPOUND according to any one of embodiments 1) to 21), for the preparation of a medicament intended for the treatment of any one of the diseases or disorders mentioned in embodiment 33).

37) A further embodiment of the invention relates to the use of COMPOUND or a pharmaceutically acceptable salt thereof, especially of a crystalline form of COMPOUND according to any one of embodiments 1) to 21), for the preparation of a medicament intended for the treatment of any one of the diseases or disorders mentioned in embodiment 34).

38) A further embodiment of the invention relates to a method for the treatment of any one of the diseases or disorders mentioned in embodiment 32), comprising administering to a patient an effective amount of COMPOUND or a pharmaceutically acceptable salt thereof, especially of a crystalline form of COMPOUND according to any one of embodiments 1) to 21), or of a pharmaceutical composition according to any one of embodiments 26) to 31).

39) A further embodiment of the invention relates to a method for the treatment of any one of the diseases or disorders mentioned in embodiment 33), comprising administering to a patient an effective amount of COMPOUND or a pharmaceutically acceptable salt thereof, especially of a crystalline form of COMPOUND according to any one of embodiments 1) to 21), or of a pharmaceutical composition according to any one of embodiments 26) to 31).

40) A further embodiment of the invention relates to a method for the treatment of any one of the diseases or disorders mentioned in embodiment 34), comprising administering to a patient an effective amount of COMPOUND or a pharmaceutically acceptable salt thereof, especially of a crystalline form of COMPOUND according to any one of embodiments 1) to 21), or of a pharmaceutical composition according to embodiments 26) to 31).

41) Yet another embodiment of the invention relates to the COMPOUND or a pharmaceutically acceptable salt thereof, especially a crystalline form of COMPOUND according to any one of embodiments 1) to 21), for use in the treatment of a disorder selected from the group consisting of chronic kidney disease (CKD), diabetes, diabetic nephropathy, diabetic retinopathy, diabetic vasculopathy, chronic heart failure and diastolic dysfunction.

42) One sub-embodiment of embodiment 41) relates to the COMPOUND or a pharmaceutically acceptable salt thereof, especially a crystalline form of COMPOUND according to any one of embodiments 1) to 21), for use in the treatment of CKD, especially CKD of stages 1 to 4 as defined by the Kidney Disease Improving Global Outcomes (KDIGO) Guidelines (and notably CKD of stage 3), and in particular CKD (notably of these stages) caused by essential hypertension.

43) Another sub-embodiment of embodiment 41) relates to the COMPOUND or a pharmaceutically acceptable salt thereof, especially a crystalline form of COMPOUND according to any one of embodiments 1) to 21), for use in the treatment of diabetes (that is, type 1 or type 2 diabetes).

44) Another sub-embodiment of embodiment 41) relates to the COMPOUND or a pharmaceutically acceptable salt thereof, especially a crystalline form of COMPOUND according to any one of embodiments 1) to 21), for use in the treatment of diabetic nephropathy.

45) Another sub-embodiment of embodiment 41) relates to the COMPOUND or a pharmaceutically acceptable salt thereof, especially a crystalline form of COMPOUND according to any one of embodiments 1) to 21), for use in the treatment of diabetic retinopathy.

46) Another sub-embodiment of embodiment 41) relates to the COMPOUND or a pharmaceutically acceptable salt thereof, especially a crystalline form of COMPOUND according to any one of embodiments 1) to 21), for use in the treatment of diabetic vasculopathy.

47) Another sub-embodiment of embodiment 41) relates to the COMPOUND or a pharmaceutically acceptable salt thereof, especially a crystalline form of COMPOUND according to any one of embodiments 1) to 21), for use in the treatment of chronic heart failure.

48) According to one variant of sub-embodiment 47), the chronic heart failure of sub-embodiment 47) will be heart failure with preserved ejection fraction.

49) According to another variant of sub-embodiment 47), the chronic heart failure of sub-embodiment 47) will be diastolic heart failure.

50) Another sub-embodiment of embodiment 41) relates to the COMPOUND or a pharmaceutically acceptable salt thereof, especially a crystalline form of COMPOUND according to any one of embodiments 1) to 21), for use in the treatment of diastolic dysfunction.

51) Preferably, the COMPOUND or a pharmaceutically acceptable salt thereof [especially a crystalline form of COMPOUND according to any one of embodiments 1) to 21)] according to any one of embodiments 41) to 50) will be comprised in a pharmaceutical unit dosage form suitable for the oral administration of 2.5 to 100 mg (in particular 5 or 10 to 50 mg, notably 25 or 50 mg) per day of the COMPOUND {5-(4-bromo-phenyl)-6-[2-(5-bromo-pyrimidin-2-yloxy)-ethoxy]-pyrimidin-4-yl}-sulfamide or of a pharmaceutically acceptable salt thereof.

52) Preferably, the COMPOUND or pharmaceutically acceptable salt thereof [especially a crystalline form of COMPOUND according to any one of embodiments 1) to 21)] according to any one of embodiments 41) to 51) will be for use in combination with an Angiotensin Converting Enzyme (ACE) inhibitor, an Angiotensin Receptor Blocker (ARB) or a Calcium Channel Blocker (CCB), or with a pharmaceutically acceptable salt of one of these.

"Angiotensin Converting Enzyme inhibitor" or "ACE inhibitor" in particular means in the present application captopril, enalapril, ramipril, quinapril, perindopril, lisinopril, imidapril or cilazapril, or a pharmaceutically acceptable salt of one of these. A preferred ACE inhibitor is enalapril or a pharmaceutically acceptable salt thereof.

"Angiotensin Receptor Blocker" or "ARB" in particular means in the present application valsartan, losartan, telmisartan, irbesartan, candesartan, olmesartan, azilsartan, or a pharmaceutically acceptable salt of one of these. A preferred ARB is valsartan or a pharmaceutically acceptable salt thereof.

"Calcium Channel Blocker" or "CCB" in particular means in the present application amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine, pranidipine, verapamil or diltiazem or a pharmaceutically acceptable salt of one of these. A preferred CCB is amlodipine or a pharmaceutically acceptable salt thereof.

Accordingly, the COMPOUND or a pharmaceutically acceptable salt thereof [especially a crystalline form of COMPOUND according to any one of embodiments 1) to 21)] according to any one of embodiments 41) to 51) can be for use in combination with an ACE inhibitor, an ARB, and/or a CCB. The corresponding combined treatment may be effected simultaneously, separately, or over a period of time (especially simultaneously).

"Simultaneously", when referring to an administration type, means in the present application that the administration type concerned consists in the administration of two or more active ingredients and/or treatments at approximately the same time; wherein it is understood that a simultaneous administration will lead to exposure of the subject to the two or more active ingredients and/or treatments at the same time. When administered simultaneously, said two or more active ingredients may be administered in a fixed dose combination, or in an equivalent non-fixed dose combination (e.g. by using two or more different pharmaceutical compositions to be administered by the same route of administration at approximately the same time), or by a non-fixed dose combination using two or more different routes of administration; wherein said administration leads to essentially simultaneous exposure of the subject to the two or more active ingredients and/or treatments. For example, when used in combination with an ACE inhibitor, an ARB, and/or a CCB, the COMPOUND would possibly be used "simultaneously". Likewise, when used in combination with a diuretic, the COMPOUND would possibly be used "simultaneously".

"Fixed dose combination", when referring to an administration type, means in the present application that the administration type concerned consists in the administration of one single pharmaceutical composition comprising the two or more active ingredients.

"Separately", when referring to an administration type, means in the present application that the administration type concerned consists in the administration of two or more active ingredients and/or treatments at different points in time; wherein it is understood that a separate administration will lead to a treatment phase (e.g. at least 1 hour, notably at least 6 hours, especially at least 12 hours) where the subject is exposed to the two or more active ingredients and/or treatments at the same time; but a separate administration may also lead to a treatment phase where for a certain period of time (e.g. at least 12 hours, especially at least one day) the subject is exposed to only one of the two or more active ingredients and/or treatments. Separate administration especially refers to situations wherein at least one of the active ingredients and/or treatments is given with a periodicity substantially different from daily (such as once or twice daily) administration (e.g. wherein one active ingredient and/or treatment is given e.g. once or twice a day, and another is given e.g. every other day, or once a week or at even longer distances).

By administration "over a period of time" is meant in the present application the subsequent administration of two or more active ingredients and/or treatments at different times. The term in particular refers to an administration method according to which the entire administration of one of the active ingredients and/or treatments is completed before the administration of the other/the others begins. In this way it is possible to administer one of the active ingredients and/or treatments for several months before administering the other active ingredient(s) and/or treatment(s).

53) Also preferably, the COMPOUND or pharmaceutically acceptable salt thereof [especially a crystalline form of COMPOUND according to any one of embodiments 1) to 21)] according to any one of embodiments 41) to 51) will be for use in combination with a diuretic (in particular for use in combination with hydrochlorothiazide (HCT)).

Accordingly, the COMPOUND or a pharmaceutically acceptable salt thereof [especially a crystalline form of COMPOUND according to any one of embodiments 1) to 21)] according to any one of embodiments 41) to 51) can be for use in combination with a diuretic (in particular for use in combination with HCT). The corresponding combined treatment may be effected simultaneously, separately, or over a period of time (especially simultaneously), as defined hereabove.

54) Yet another embodiment of the invention relates to the use of the COMPOUND or of a pharmaceutically acceptable salt thereof [especially of a crystalline form of COMPOUND according to any one of embodiments 1) to 21)], for the manufacture of a medicament for use in the treatment of a disorder selected from the group consisting of chronic kidney disease (CKD), diabetes, diabetic nephropathy, diabetic retinopathy, diabetic vasculopathy, chronic heart failure and diastolic dysfunction.

55) One sub-embodiment of embodiment 54) relates to the use according to embodiment 54) which is for the manufacture of a medicament for use in the treatment of CKD, especially CKD of stages 1 to 4 as defined by the Kidney Disease Improving Global Outcomes (KDIGO) Guidelines (and notably CKD of stage 3), and in particular CKD (notably of these stages) caused by essential hypertension.

56) Another sub-embodiment of embodiment 54) relates to the use according to embodiment 54) which is for the manufacture of a medicament for use in the treatment of diabetes (that is, type 1 or type 2 diabetes).

57) Another sub-embodiment of embodiment 54) relates to the use according to embodiment 54) which is for the manufacture of a medicament for use in the treatment of diabetic nephropathy.

58) Another sub-embodiment of embodiment 54) relates to the use according to embodiment 54) which is for the manufacture of a medicament for use in the treatment of diabetic retinopathy.

59) Another sub-embodiment of embodiment 54) relates to the use according to embodiment 54) which is for the manufacture of a medicament for use in the treatment of diabetic vasculopathy.

60) Another sub-embodiment of embodiment 54) relates to the use according to embodiment 54) which is for the manufacture of a medicament for use in the treatment of chronic heart failure.

61) According to one variant of sub-embodiment 60), the chronic heart failure of sub-embodiment 60) will be heart failure with preserved ejection fraction.

62) According to another variant of sub-embodiment 60), the chronic heart failure of sub-embodiment 60) will be diastolic heart failure.

63) Another sub-embodiment of embodiment 54) relates to the use according to embodiment 54) which is for the manufacture of a medicament for use in the treatment of diastolic dysfunction.

64) Preferably, the use according to any one of embodiments 54) to 63) will be such that it is for the manufacture of a pharmaceutical unit dosage form suitable for the oral administration of 2.5 to 100 mg (in particular 5 or 10 to 50 mg, notably 25 or 50 mg) per day of the COMPOUND or of a pharmaceutically acceptable salt thereof [especially of a crystalline form of COMPOUND according to any one of embodiments 1) to 21)].

65) Preferably, the use according to any one of embodiments 54) to 64) will be for the manufacture of a medicament for use in combination with an Angiotensin Converting Enzyme (ACE) inhibitor, an Angiotensin Receptor Blocker (ARB) or a Calcium Channel Blocker (CCB) or with a pharmaceutically acceptable salt of one of these.

Accordingly, the use according to any one of embodiments 54) to 64) can be for the manufacture of a medicament for use in combination with an ACE inhibitor, an ARB or a CCB or with a pharmaceutically acceptable salt of one of these. The corresponding combined treatment may be effected simultaneously, separately, or over a period of time (especially simultaneously).

66) Also preferably, the use according to any one of embodiments 54) to 64) will be for the manufacture of a medicament for use in combination with a diuretic (in particular for the manufacture of a medicament for use in combination with hydrochlorothiazide (HCT)).

Accordingly, the use according to any one of embodiments 54) to 64) can be for the manufacture of a medicament for use in combination with a diuretic (in particular for the manufacture of a medicament for use in combination with HCT). The corresponding combined treatment may be effected simultaneously, separately, or over a period of time (especially simultaneously), as defined hereabove.

67) Yet another embodiment of the invention relates to a method for treating a disorder selected from the group consisting of chronic kidney disease (CKD), diabetes, diabetic nephropathy, diabetic retinopathy, diabetic vasculopathy, chronic heart failure and diastolic dysfunction in a patient, said method comprising the administration of a therapeutically effective amount of the COMPOUND or of a pharmaceutically acceptable salt thereof [especially of a crystalline form of COMPOUND according to any one of embodiments 1) to 21)], to a patient in need thereof.

68) One sub-embodiment of embodiment 67) relates to the method according to embodiment 67) which is for treating CKD in a patient, especially CKD of stages 1 to 4 as defined by the Kidney Disease Improving Global Outcomes (KDIGO) Guidelines (and notably CKD of stage 3), and in particular CKD (notably of these stages) caused by essential hypertension.

69) Another sub-embodiment of embodiment 67) relates to the method according to embodiment 67) which is for treating diabetes (that is, type 1 or type 2 diabetes).

70) Another sub-embodiment of embodiment 67) relates to the method according to embodiment 67) which is for treating diabetic nephropathy.

71) Another sub-embodiment of embodiment 67) relates to the method according to embodiment 67) which is for treating diabetic retinopathy.

72) Another sub-embodiment of embodiment 67) relates to the method according to embodiment 67) which is for treating diabetic vasculopathy.

73) Another sub-embodiment of embodiment 67) relates to the method according to embodiment 67) which is for treating chronic heart failure.

74) According to one variant of sub-embodiment 73), the chronic heart failure of sub-embodiment 73) will be heart failure with preserved ejection fraction.

75) According to another variant of sub-embodiment 73), the chronic heart failure of sub-embodiment 73) will be diastolic heart failure.

76) Another sub-embodiment of embodiment 67) relates to the method according to embodiment 67) which is for treating diastolic dysfunction.

77) Preferably, the method according to any one of embodiments 67) to 76) will be such that a dose of 2.5 to 100 mg (in particular 5 or 10 to 50 mg, notably 25 or 50 mg) per day of the COMPOUND or of a pharmaceutically acceptable salt thereof [especially of a crystalline form of COMPOUND according to any one of embodiments 1) to 21)] is administered orally to a patient in need thereof.

78) Preferably, the method according to any one of embodiments 67) to 77) will such that a therapeutically effective amount of the COMPOUND or of a pharmaceutically acceptable salt thereof [especially of a crystalline form of COMPOUND according to any one of embodiments 1) to 21)] is administered in combination with a therapeutically effective amount of an Angiotensin Converting Enzyme (ACE) inhibitor, an Angiotensin Receptor Blocker (ARB) or a Calcium Channel Blocker (CCB) or of a pharmaceutically acceptable salt of one of these.

Accordingly, the method according to any one of embodiments 67) to 77) can be such that a therapeutically effective amount of the COMPOUND or of a pharmaceutically acceptable salt thereof [especially of a crystalline form of COMPOUND according to any one of embodiments 1) to 21)] is administered in combination with a therapeutically effective amount of an ACE inhibitor, an ARB or a CCB or of a pharmaceutically acceptable salt of one of these. The corresponding combined treatment may be effected simultaneously, separately, or over a period of time (especially simultaneously).

79) Also preferably, the method according to any one of embodiments 67) to 77) will such that a therapeutically effective amount of the COMPOUND or of a pharmaceutically acceptable salt thereof [especially of a crystalline form of COMPOUND according to any one of embodiments 1) to 21)] is administered in combination with a therapeutically effective amount of a diuretic (in particular in combination with a therapeutically effective amount of hydrochlorothiazide (HCT)).

Accordingly, the method according to any one of embodiments 67) to 77) can be such that a therapeutically effective amount of the COMPOUND or of a pharmaceutically acceptable salt thereof [especially of a crystalline form of COMPOUND according to any one of embodiments 1) to 21)] is administered in combination with a therapeutically effective amount of a diuretic (in particular in combination with a therapeutically effective amount of HCT). The corresponding combined treatment may be effected simultaneously, separately, or over a period of time (especially simultaneously).

Particular embodiments of the invention are described in the following Examples, which serve to illustrate the invention in more detail without limiting its scope in any way.

EXPERIMENTAL PROCEDURES

Abbreviations

The following abbreviations are used throughout the specification and the examples:
Ac acetyl
AcOH acetic acid
aq. aqueous
DCM dichloromethane
DMSO dimethylsulfoxide
EtOAc ethyl acetate
eq. equivalent(s)
FTIR Fourier Transform Infrared Spectroscopy or Spectrum
HPLC High Performance Liquid Chromatography
iPrOAc isopropyl acetate
MeOH methanol
MIBK methyl iso-butyl ketone
org. organic
rt room temperature
THF tetrahydrofuran
vol. volume(s)
w/w weight-per-weight ratio
wt. weight unit
XRPD X-ray powder diffraction

EXAMPLES

Method for Obtaining XRPD Patterns

All XRPD patterns for the solid forms described herein have been obtained as described hereafter. X-ray powder diffraction patterns were collected on a Bruker D8 Advance X-ray diffractometer equipped with a Lynxeye detector operated with CuKα-radiation in reflection mode (coupled two Theta/Theta). Typically, the X-ray tube was run at of 40 kV/40 mA. A step size of 0.02° (2θ) and a step time of 76.8 see over a scanning range of 3-500 in 2θ were applied. The divergence slit was set to fixed 0.3. Powders were slightly pressed into a silicon single crystal sample holder with depth of 0.5 mm and samples were rotated in their own plane during the measurement. Diffraction data are reported using combined Cu Kα1 and Kα2 radiation, without Kα2 stripping. The accuracy of the 2θ values as provided herein is in the range of +/−0.1-0.2° as it is generally the case for conventionally recorded X-ray powder diffraction patterns.

Gravimetric Vapour Sorption (GVS)

Measurements are performed on a multi sample instrument SPS-100n (Projekt Messtechnik, Ulm, Germany) operated in stepping mode at 25° C. The sample is allowed to equilibrate at 40% RH before starting a pre-defined humidity program (40-0-95-0-95-40% RH, steps of 5% ΔRH and with a maximal equilibration time of 24 hours per step are applied. About 20 to 30 mg of each sample is used.

The hygroscopic classification is done according to the European Pharmacopeia Technical Guide (1999, page 86), e.g., slightly hygroscopic: increase in mass is less than 2% and equal to or greater than 0.2% mass/mass; hygroscopic: increase in mass is less than 15% and equal to or greater than 2% mass/mass. The mass change between 40% relative humidity and 80% relative humidity in the first adsorption scan is considered.

Differential Scanning Calorimetry (DSC)

DSC data are collected on a Mettler Toledo STARe System (DSC822e module, measuring cell with ceramic sensor and STAR software version 9.20) equipped with a 34-position auto-sampler. The instrument is calibrated for energy and temperature using certified indium. Typically, 1-5 mg of each sample, in an automatically pierced aluminium pan, is heated at 10° C. min-1, unless stated otherwise, from −20° C. to 280° C. A nitrogen purge at 20 mL min-1 is maintained over the sample. Peak temperatures are reported for melting points.

Thermogravimetric Analysis (TGA)

TGA data are collected on a Mettler Toledo STARe System (TGA851e module and STAR software version 9.20) equipped with a 34 position auto-sampler. Typically about 5 mg of a sample, in an automatically pierced aluminium pan, is heated at 10° C. min$^{-1}$, unless stated otherwise, from 30° C. to 250° C. A nitrogen purge at 10 mL min−1 is maintained over the sample.

Example 1: Form A 1.1. A 3 L double jacketed reactor was charged with 5-(4-bromophenyl)-4-(2-((5-bromopyrimidin-2-yl)oxy) ethoxy)-6-fluoropyrimidine (100 g, 0.213 mol, 1 eq. (WO2015/121397)), sulfamide (40.9 g, 0.425 mol, 2.0 eq.), K$_2$CO$_3$ (147 g, 1.06 mol, 5 eq.) and DMSO (500 mL, 5 vol.) doped with water (2 mL, 0.111 mol, 0.5 eq.). The heterogeneous mixture was heated to 70° C. during ca. 3 h, after which time complete conversion was observed. After cooling to 20° C., most of the inorganic salt freight was removed by filtration. The filter cake was washed with EtOAc/iPrOAc 1:1 (300 mL, 3 vol.). Celite (100 g, 1 wt.) topped with a layer of charcoal (20 g, 0.2 wt.) was preconditioned with EtOAc/iPrOAc 1:1 (500 mL, 5 vol.) (filtrate discarded). The reaction mixture was filtered over this cake and rinsed with EtOAc/iPrOAc 1:1 (300 mL, 3 vol.). Then 1M aq. NaOAc solution (500 mL, 0.5 mol, 2.3 eq, 5 vol.) was added while keeping the temperature at 25-35° C. The aq. phase was washed a second time with EtOAc/iPrOAc 1:1 (500 mL, 5 vol.). To the aq. phase, 1M H$_2$SO$_4$ (200 mL, 0.2 mol, 1 eq., 2 vol.) was added during 1 h at 25-30° C. Crystallization started at pH 8.5-8.0. The crude product was filtered off as XRPD pattern form K (DMSO solvate) or a mixture of form A and form K. It was washed twice with water (2×1000 mL, 2×10 vol.). The solid was slurried in water (1000 mL, 10 vol.) at rt for 3 h. The solid was filtered off and slurried a second time in water (1000 mL, 10 vol.) at rt for 3 h. After washing with water (1000 mL, 10 vol.), the pure product was dried in vacuum at 40° C. to afford {5-(4-bromophenyl)-6-[2-(5-bromo-pyrimidin-2-yloxy)-ethoxy]-pyrimidin-4-yl}-sulfamide as a white to off-white solid (75 g, 65% yield, XRPD pattern form A).

1.2. A reactor (200 L Hastelloy) was charged with 5-(4-bromophenyl)-4-(2-((5-bromopyrimidin-2-yl)oxy) ethoxy)-6 fluoropyrimidine (24.2 kg, 51.5 mol), sulfamide (9.7 kg, 100.9 mol, 1.96 eq.), potassium carbonate (35.5 kg, 256.9 mol, 5.0 eq.), DMSO (133 kg, 5 vol.) and water (490 g, 27.2 mol, 0.53 eq.). The contents of the reactor were heated to 70-75° C. Monitoring by HPLC showed complete conversion in 4 hours. The contents were cooled to 20-25° C. and the solids were centrifuged off. Each load was washed with EtOAc/iPrOAc 1:1 (65 kg, 3vol.). The filtrate was re-charged in the reactor and charcoal (2.4 kg, 10% w/w) and Celite® (4.8 kg, 20% w/w) were added. The contents were agitated for 1 h at 15-20° C. and filtered through a cartridge filter back into the reactor. The filters were rinsed with EtOAc/iPrOAc 1:1 (43 kg, 2 vol.). NaOAc (8% in water) (124 kg, 5 vol.) was added over 2 h, keeping the temperature below 25° C. After phase separation, the aq. layer was washed with EtOAc/iPrOAc 1:1 (109 kg, 5 vol.) at 20-25° C. Sulfuric acid (5% in water; 64 L, 32.6 mol, 0.63 eq.) was added to the aq. layer at 25-30° C. over 2 hours to reach pH 6.4. The contents were then cooled to 15-20° C. for 1 h. The solids were filtered off and washed twice with water (2×24 L, 2×1 vol.). The solid was slurried twice in water (2×242 kg, 2×10 vol.) at 15-20° C. for 3 hours each, filtered and dried, to yield 5-(4-bromo-phenyl)-6-[2-(5-bromo-pyrimidin-2-yloxy)-ethoxy]-pyrimidin-4-yl}-sulfamide as a white solid (21.6 kg, 77% yield, XRPD pattern Form A).

Example 2: Form B (DCM Solvate of the COMPOUND)

5-(4-bromophenyl)-4-(2-((5-bromopyrimidin-2-yl)oxy) ethoxy)-6 fluoropyrimidine (10.0 g, 21.3 mmol, 1.00 eq.), sulfamide (4.1 g, 42.5 mmol, 2.0 eq.) and K$_2$CO$_3$ (14.7 g, 106 mmol, 5.0 eq.) were suspended in DMSO (50 mL, 5 vol.) and heated to 70° C. for 5 h. The mixture was cooled to rt and EtOAc (40 mL, 4 vol.) followed by water (100 mL, 10 vol.) were added. After separation of the layers (org. phase discarded), the aq. phase was extracted with DCM (100 mL, 10 vol.). The DCM layer was acidified from pH 11.5 to pH 7.0 with conc. AcOH (3 mL, 52 mmol, 2.5 eq.), resulting in crystallization of the product. The suspension was cooled to 0° C. for 1 h, then to −5° C. for 15 min. The solid was filtered, washed with cold DCM (10 mL, 1 vol.) and dried to yield a DCM solvate of {5-(4-bromo-phenyl)-6-[2-(5-bromo-pyrimidin-2-yloxy)-ethoxy]-pyrimidin-4-yl}-sulfamide in Form B as a white solid (9.8 g, 84% yield).

Example 3: Form C 0.2 mL of a stock solution of {5-(4-bromo-phenyl)-6-[2-(5-bromo-pyrimidin-2-yloxy)-ethoxy]-pyrimidin-4-yl}-sulfamide dissolved in THF at 50 mg/mL was dispensed to 3 vials. The solvent was evaporated for 90 min in a Combidancer device from Hettich AG (Bach, Switzerland) operated at 35° C. and 200 mbar. Immediately thereafter 0.015 mL of MeOH for the first vial, EtOH for the second vial and iPrOH for the third vial was added and the vials were allowed to stand closed for 3 days. Solid residue of {5-(4-bromo-phenyl)-6-[2-(5-bromo-pyrimidin-2-yloxy)-ethoxy]-pyrimidin-4-yl}-sulfamide in Form C was obtained for each of these solvents.

Example 4: Form D 4.1. A reactor was charged with sulfamide (2.00 eq.), $K_2CO_3$ (5.00 eq.), 5-(4-bromophenyl)-4-(2-((5-bromopyrimidin-2-yl)oxy)ethoxy)-6-fluoropyrimidine (1.00 eq.), DMSO (5.0 vol.) and water (0.02 vol.). The mixture was heated to 75° C. for 2 h. After cooling to 23° C., the suspension was filtered and rinsed with EtOAc/iPrOAc 1:1 (5.5 vol.) through the reactor. The filtrate was again filtered through an in-line filter and rinsed with EtOAc/iPrOAc 1:1 (1.5 vol.). A solution of 1M NaOAc in water (5.0 vol.) was added at 27° C., and the layers were separated. The aq. phase was washed with EtOAc/iPrOAc 1:1 (5.0 vol.). The aq. phase was acidified to pH 5.8 using 0.5M $H_2SO_4$ in water (2.35 vol.) over 2.5 h, leading to crystallization. After 1 h stirring at 20° C., the suspension was filtered and washed with water (2×10 vol.). The solid was slurried twice in water (2×10 vol.) at 20° C. for 3 h each, filtered, washed with water (10 vol.) and dried to give {5-(4-bromo-phenyl)-6-[2-(5-bromo-pyrimidin-2-yloxy)-ethoxy]-pyrimidin-4-yl}-sulfamide in Form D.

4.2. 50 mg of {5-(4-bromo-phenyl)-6-[2-(5-bromo-pyrimidin-2-yloxy)-ethoxy]-pyrimidin-4-yl}-sulfamide in Form A was dissolved in 3 mL methyl-ethylketone in a new 7 mL glass vial. After sonication in an ultrasound bath for 1 min, the vial was allowed to stand open at rt for 3 days. The solid residue was {5-(4-bromo-phenyl)-6-[2-(5-bromo-pyrimidin-2-yloxy)-ethoxy]-pyrimidin-4-yl}-sulfamide in Form D.

Example 5: Form E (MeCN Solvate of the COMPOUND)

{5-(4-bromo-phenyl)-6-[2-(5-bromo-pyrimidin-2-yloxy)-ethoxy]-pyrimidin-4-yl}-sulfamide in Form A was heated to reflux in 10 volumes of MeCN. After 10 min it was allowed to cool down to 20° C. within 1 h (heating bath removed). It was filtered off and dried under reduced pressure and 45° C. Solid residue was a MeCN solvate of {5-(4-bromo-phenyl)-6-[2-(5-bromo-pyrimidin-2-yloxy)-ethoxy]-pyrimidin-4-yl}-sulfamide in Form E.

Example 6: Form J

The DCM solvate of {5-(4-bromo-phenyl)-6-[2-(5-bromo-pyrimidin-2-yloxy)-ethoxy]-pyrimidin-4-yl}-sulfamide Form B (9.4 g, 17.2 mmol, 1.00 eq.) was dissolved in DMSO (19 mL, 2 vol.). The solution was added into $H_2O$ (94 mL, 10 vol.) and stirred at rt for 5 min. The resulting suspension was filtered, washed twice with $H_2O$ (2×94 mL, 2×10 vol.) and dried to provide {5-(4-bromo-phenyl)-6-[2-(5-bromo-pyrimidin-2-yloxy)-ethoxy]-pyrimidin-4-yl}-sulfamide Form J as a white solid (6.8 g, 72% yield).

Example 7: Form K (DMSO Solvate of the COMPOUND)

7.1. {5-(4-bromo-phenyl)-6-[2-(5-bromo-pyrimidin-2-yloxy)-ethoxy]-pyrimidin-4-yl}-sulfamide Form A (1.00 g, 1.83 mmol, 1.00 eq.) was dissolved in DMSO (2 mL, 2 vol.). To this solution, 10% $H_2O$ in DMSO (10 mL, 10 vol.) was added slowly, followed by pure $H_2O$ (2 mL, 2 vol.). Seeding with form K triggered crystallization of the product. The suspension was filtered, washed with $H_2O$ (5×10 mL, 5×10 vol.) and dried to give a DMSO solvate {5-(4-bromo-phenyl)-6-[2-(5-bromo-pyrimidin-2-yloxy)-ethoxy]-pyrimidin-4-yl}-sulfamide in Form K as a white solid (0.95 g, 95% yield).

7.2. 5-(4-bromophenyl)-4-(2-((5-bromopyrimidin-2-yl)oxy)ethoxy)-6-fluoropyrimidine (10.0 g, 21.3 mmol, 1.00 eq.), sulfamide (4.1 g, 42.5 mmol, 2.0 eq.) and $K_2CO_3$ (14.7 g, 106 mmol, 5.0 eq.) were suspended in DMSO (50 mL, 5 vol.) and heated to 50° C. for 20 h. The mixture was cooled to rt and MIBK (100 mL, 10 vol.) followed by water (100 mL, 10 vol.) were added. After separation of the layers (org. phase discarded), the aq. phase was acidified from pH 11.4 to pH 6.5 with conc. AcOH (4 mL, 70 mmol, 3.3 eq.), resulting in crystallization of the product. The solid was filtered, washed with water (4×50 mL, 4×5 vol.) and dried to afford a DMSO solvate of {5-(4-bromo-phenyl)-6-[2-(5-bromo-pyrimidin-2-yloxy)-ethoxy]-pyrimidin-4-yl}-sulfamide in Form K as a beige solid (10.4 g, 90% yield).

Example 8: Form L (EtOH Solvate of the COMPOUND)

The DMSO solvate of {5-(4-bromo-phenyl)-6-[2-(5-bromo-pyrimidin-2-yloxy)-ethoxy]-pyrimidin-4-yl}-sulfamide Form K (100 mg, 0.183 mmol, 1.00 eq.) was slurried in EtOH (0.5 mL, 5 vol.) at rt for 4 h. The suspension was filtered, washed twice with $H_2O$ (2×0.5 mL, 2×5 vol.) and dried to afford an EtOH solvate of {5-(4-bromo-phenyl)-6-[2-(5-bromo-pyrimidin-2-yloxy)-ethoxy]-pyrimidin-4-yl}-sulfamide in Form L as a white solid (40 mg, 40% yield).

Example 9: ACT-132577 Tablets

Tablets containing each 50 mg of COMPOUND can be prepared using a wet granulation process. The tablet composition is the following:

| ACT-132577 tablets (250 mg) | | | |
|---|---|---|---|
| | Material (Chemical name) | mg/ tablet | Weight %/ tablet |
| Intra-granular | COMPOUND (amorphous, or solid form A or solid form C, as described herein) | 50.00 | 20.00 |
| | Microcrystalline cellulose | 61.50 | 24.60 |
| | Lactose (200M) | 122.25 | 48.90 |
| | Hydroxypropylcellulose | 5.50 | 2.20 |
| | Croscarmellose sodium | 4.50 | 1.80 |
| | Water | qs | qs |
| Extra-granular | Croscarmellose sodium | 5.00 | 2.00 |
| | Magnesium stearate | 1.25 | 0.50 |
| | Total | 250.00 | 100.00 | qs = quantity sufficient

Preferably, COMPOUND in crystalline Form A (as described herein) will be used for making the tablets.

Example 10: ACT-132577 Tablets

The tablets of Example 9 can be coated with a layer of Aquapolish® white MS or Aquapolish® white PVA (coating manufacturer: Biogrund).

Example 11: ACT-132577 Tablets

Tablets containing each 50 mg of COMPOUND can be prepared using a wet granulation process. The tablet composition is the following:

| ACT-132577 tablets (250 mg) | | | |
|---|---|---|---|
| | Material (Chemical name) | mg/ tablet | Weight %/ tablet |
| Intra-granular | COMPOUND (amorphous, or solid form A or solid form C, as described herein) | 50.00 | 20.00 |
| | Microcrystalline cellulose | 61.25 | 24.50 |
| | Lactose (200M) | 122.50 | 49.00 |
| | Hydroxypropylcellulose | 5.00 | 2.00 |
| | Croscarmellose sodium | 5.00 | 2.00 |
| | Water | qs | qs |
| Extra-granular | Croscarmellose sodium | 5.00 | 2.00 |
| | Magnesium stearate | 1.25 | 0.50 |
| | Total | 250.00 | 100.00 | qs = quantity sufficient

Preferably, COMPOUND in crystalline Form A (as described herein) will be used for making the tablets.

Example 12

The tablets of Example 11 can be coated with a layer of Aquapolish® white MS or Aquapolish® white PVA (coating manufacturer: Biogrund).

Example 13: ACT-132577 Tablets

Tablets containing each 12.5 mg of COMPOUND can be prepared using a wet granulation process. The tablet composition is the following:

| ACT-132577 tablets (100 mg) | | | |
|---|---|---|---|
| | Material (Chemical name) | mg/ tablet | Weight %/ tablet |
| Intra-granular | COMPOUND (amorphous, or solid form A or solid form C, as described herein) | 12.50 | 12.50 |
| | Microcrystalline cellulose | 27.00 | 27.00 |
| | Lactose (200M) | 54.00 | 54.00 |
| | Hydroxypropylcellulose | 2.00 | 2.00 |
| | Croscarmellose sodium | 2.00 | 2.00 |
| | Water | qs | qs |
| Extra-granular | Croscarmellose sodium | 2.00 | 2.00 |
| | Magnesium stearate | 0.50 | 0.50 |
| | Total | 100.00 | 100.00 | qs = quantity sufficient

Preferably, COMPOUND in crystalline Form A (as described herein) will be used for making the tablets.

Example 14: ACT-132577 Tablets

The tablets of Example 13 can be coated with a layer of Aquapolish® white MS or Aquapolish® white PVA (coating manufacturer: Biogrund).

Example 15: ACT-132577 Tablets

Tablets containing each 12.5 mg of COMPOUND can be prepared using a wet granulation process. The tablet composition is the following:

| ACT-132577 tablets (100 mg) | | | |
|---|---|---|---|
| | Material (Chemical name) | mg/ tablet | Weight %/ tablet |
| Intra-granular | COMPOUND (amorphous, or solid form A or solid form C, as described herein) | 12.50 | 12.50 |
| | Microcrystalline cellulose | 27.50 | 27.50 |
| | Lactose (200M) | 53.50 | 53.50 |
| | Hydroxypropylcellulose | 2.20 | 2.20 |
| | Croscarmellose sodium | 1.80 | 1.80 |
| | Water | qs | qs |
| Extra-granular | Croscarmellose sodium | 2.00 | 2.00 |
| | Magnesium stearate | 0.50 | 0.50 |
| | Total | 100.00 | 100.00 | qs = quantity sufficient

Preferably, COMPOUND in crystalline Form A (as described herein) will be used for making the tablets.

Example 16: ACT-132577 Tablets

The tablets of Example 15 can be coated with a layer of Aquapolish® white MS or Aquapolish® white PVA (coating manufacturer: Biogrund).

Properties of the Crystalline Forms

Storage at Room Temperature

A sample of Form A crystals of the COMPOUND (as obtained according to Example 1 above) has been stored at a temperature of 20-25° C. at 92% relative humidity for 2 months. X-ray powder diffraction performed on that sample at the end of the 2 months showed that the sample was still consisting only in Form A crystals of the COMPOUND. The same result was obtained after storage for 8 weeks under the above coditions. HPLC control of the sample after 8 weeks storage revealed no significant change in peak area %, i.e. no significant degradation was observed under such conditions.

A sample of Form B crystals of a dichloromethane solvate of the COMPOUND (as obtained according to Example 2 above) has been stored in a closed vial (20 mg of Form B crystals being placed in a closed 4 mL vial) at a temperature of 20-25° C. for about 3 weeks. X-ray powder diffraction performed on that sample at the end of the 3 weeks showed that the Form B crystals were transformed into Form A crystals of the COMPOUND.

A sample of Form K crystals of a dimethylsulfoxide solvate of the COMPOUND (as obtained according to Example 7 above) has been stored in a closed vial (20 mg of Form K crystals being placed in a closed 4 mL vial) at a temperature of 20-25° C. for about 3 weeks. X-ray powder diffraction performed on that sample at the end of the 3 weeks showed that the Form K crystals were transformed into Form A crystals of the COMPOUND.

DSC

Form A of COMPOUND (as obtained by example 1) melts and decomposes concomitantly. By DSC an endothermic/exothermic signal is observed, with a peak of the endotherm observed at about 159° C.

Form C of COMPOUND (as obtained by example 3) melts and decomposes concomitantly. By DSC an endothermic/exothermic signal is observed, with a peak of the endotherm observed at about 153° C.

Hygroscopicity

Form A e.g. as obtained from Example 1 is considered to be non-hygroscopic as determined by gravimetric vapor sorption (GVS) (see FIG. 19).

Form C e.g. as obtained from Example 3 is considered to be slightly hygroscopic as determined by gravimetric vapor sorption (GVS) (see FIG. 20).

EXAMPLES OF THERAPEUTIC USES OF APROCITENTAN

Example A: Acute Effects of COMPOUND in Dahl Salt-Sensitive Rats

The acute effects of COMPOUND on blood pressure, in particular on mean arterial blood pressure (hereafter "MAP"), and heart rate (hereafter "HR") were evaluated by means of telemetry in conscious, male hypertensive Dahl salt-sensitive rats (hereafter "Dahl-S rats"-see details about this model in Rapp, *Hypertension* (1982), 4, 753-763).

Elevated blood pressure is induced in Dahl-S rats by providing 1% sodium chloride in drinking water. Groups of 6-7 Dahl-S rats were used for the vehicle (7.5% gelatin aquous solution) and each dose of COMPOUND tested (0.3, 1, 3, 10, 30, 100, and 300 mg/kg). Effects of COMPOUND on HR and MAP were calculated for individual animals relative to the 24 h period before administering. The results obtained regarding MAP (maximal MAP decrease observed over 6 consecutive hours) are summarised in FIG. 9 (data are presented as mean±standard error of the mean). In summary, a dose of 10 mg/kg COMPOUND decreased MAP by 19±4 mm Hg in Dahl-S rats. In contrast to MAP, HR was not affected.

Example B: Acute Effects of COMPOUND in Deoxycorticosterone Acetate Salt Rats The acute effects of COMPOUND on blood pressure, in particular on mean arterial blood pressure (hereafter "MAP"), and heart rate (hereafter "HR") were evaluated by means of telemetry in conscious, male hypertensive deoxycorticosterone acetate salt rats (hereafter "DOCA-salt rats"—see details about this model in Gavras et al., *Circ. Res.* (1975), 36, 300-309).

In the DOCA-salt rats, hypertension is induced by the combination of unilateral nephrectomy, implantation of pellets of the mineralocorticoid analog DOCA, and provision of 1% sodium chloride in drinking water. Groups of 6-11 DOCA-salt rats were used for the vehicle (7.5% gelatin aquous solution) and each dose of COMPOUND tested (0.3, 1, 3, 10, 30, 100, and 300 mg/kg). Effects of COMPOUND on HR and MAP were calculated for individual animals relative to the 24 h period before administering. The results obtained regarding MAP (maximal MAP decrease observed over 6 consecutive hours) are summarised in FIG. 10 (data are presented as mean±standard error of the mean). In summary, a dose of 10 mg/kg COMPOUND decreased MAP by 29±6 mm Hg in DOCA-salt rats. In contrast to MAP, HR was not affected.

Example C: Acute Effects of COMPOUND in Spontaneaously Hypertensive Rats

The acute effects of COMPOUND on blood pressure, in particular on mean arterial blood pressure (hereafter "MAP"), and heart rate (hereafter "HR") were evaluated by means of telemetry in conscious, male spontancaously hypertensive rats (hereafter "SHRs"—see details about this model in Atanur et al., *Genome Res.* (2010), 20, 791-803).

Groups of 4-6 SHRs were used for the vehicle (7.5% gelatin aquous solution) and each dose of COMPOUND tested (1, 3, 10, 30, 100, and 300 mg/kg). Effects of COMPOUND on HR and MAP were calculated for individual animals relative to the 24 h period before administering. The results obtained regarding MAP (maximal MAP decrease observed over 6 consecutive hours) are summarised in FIG. 11 (data are presented as mean±standard error of the mean). In summary, a dose of 100 mg/kg COMPOUND decreased MAP by 18±4 mm Hg in SHRs. In contrast to MAP, HR was not affected.

Example D: Acute Effects of COMPOUND, Alone or in Combination with Valsartan, in Spontaneaously Hypertensive Rats The acute effects of COMPOUND administered orally at a single dose of 100 mg/kg on blood pressure, in particular on mean arterial blood pressure (hereafter "MAP"), and heart rate (hereafter "HR"), with COMPOUND being used either alone or in combination with valsartan administered orally at a single dose of 10 mg/kg, were evaluated by means of telemetry in conscious, male spontaneaously hypertensive rats (hereafter "SHRs"—see details about this model in Atanur et al., *Genome Res.* (2010), 20, 791-803).

6 SHRs per treatment group were used for this test. The results obtained regarding MAP are summarised in FIG. 12 wherein each data point is presented as a 6-hour mean (NB: the expected additive effect of the combination of the two drugs, referred to as "Predicted additive effect", was calculated by adding the decreases in blood pressure values obtained after administration of each compound separately); the vehicle (7.5% gelatin aquous solution) treatment had no effect on MAP or HR and the results obtained are therefore not represented in the figure. In brief, co-administration of COMPOUND and valsartan decreased MAP beyond the predicted (calculated) values, demonstrating synergism between the two molecules. In contrast to MAP, HR was not affected in any of the treatment groups.

Example E: Acute Effects of COMPOUND, Alone or in Combination with Valsartan, in Deoxycorticosterone Acetate Salt Rats The acute effects of COMPOUND administered orally at a single dose of 10 mg/kg on blood pressure, in particular on mean arterial blood pressure (hereafter "MAP"), and heart rate (hereafter "HR"), with COMPOUND being used either alone or in combination with valsartan administered orally at a single dose of 30 mg/kg, were evaluated by means of telemetry in conscious, male hypertensive deoxycorticosterone acetate salt rats (hereafter "DOCA-salt rats"—see details about this model in Gavras et al., *Circ. Res.* (1975), 36, 300-309).

In the DOCA-salt rats, hypertension is induced by the combination of unilateral nephrectomy, implantation of pellets of the mineralocorticoid analog DOCA, and provision of 1% sodium chloride in drinking water. 7-8 DOCA-salt rats per treatment group were used for this test. The results obtained regarding MAP are summarised in FIG. 13 wherein each data point is presented as a 6-hour mean (NB: the expected additive effect of the combination of the two drugs, referred to as "Predicted additive effect", was calculated by adding the decreases in blood pressure values obtained after administration of each compound separately); the vehicle (4% gelatin aquous solution) treatment had no effect on MAP or HR and the results obtained are therefore not represented in the figure. In brief, co-administration of COMPOUND and valsartan decreased MAP beyond the predicted (calculated) values, demonstrating synergism between the two molecules. In contrast to MAP, HR was not affected in any of the treatment groups.

Example F: Acute Effects of COMPOUND, Alone or in Combination with Enalapril, in Spontaneaously Hypertensive Rats The acute effects of COMPOUND administered orally at a single dose of 100 mg/kg on blood pressure, in particular on mean arterial blood pressure (hereafter "MAP"), and heart rate (hereafter "HR"), with COMPOUND being used either alone or in combination with enalapril administered orally at a single dose of 3 mg/kg, were evaluated by means of telemetry in conscious, male spontaneaously hypertensive rats (hereafter "SHRs"—see details about this model in Atanur et al., *Genome Res.* (2010), 20, 791-803).

7 SHRs per treatment group were used for this test. The results obtained regarding MAP are summarised in FIG. 14 wherein each data point is presented as a 6-hour mean (NB: the expected additive effect of the combination of the two drugs, referred to as "Predicted additive effect", was calculated by adding the decreases in blood pressure values obtained after administration of each compound separately); the vehicle (4% gelatin aquous solution) treatment had no effect on MAP or HR and the results obtained are therefore not represented in the figure. In brief, co-administration of COMPOUND and enalapril decreased MAP beyond the predicted (calculated) values, demonstrating synergism between the two molecules. In contrast to MAP, HR was not affected in any of the treatment groups.

Example G: Acute Effects of COMPOUND, Alone or in Combination with Amlodipine, in Deoxycorticosterone Acetate Salt Rats The acute effects of COMPOUND administered orally at a single dose of 10 mg/kg on blood pressure, in particular on mean arterial blood pressure (hereafter "MAP"), and heart rate (hereafter "HR"), with COMPOUND being used either alone or in combination with amlodipine administered orally at a single dose of 1 mg/kg, were evaluated by means of telemetry in conscious, male hypertensive deoxycorticosterone acetate salt rats (hereafter "DOCA-salt rats"—see details about this model in Gavras et al., *Circ. Res.* (1975), 36, 300-309).

In the DOCA-salt rats, hypertension is induced by the combination of unilateral nephrectomy, implantation of pellets of the mincralocorticoid analog DOCA, and provision of 1% sodium chloride in drinking water. 6-8 DOCA-salt rats per treatment group were used for this test. The results obtained regarding MAP are summarised in FIG. 15 wherein each data point is presented as a 6-hour mean (NB: the expected additive effect of the combination of the two drugs, referred to as "Predicted additive effect", was calculated by adding the decreases in blood pressure values obtained after administration of each compound separately); the vehicle (4% gelatin aquous solution) treatment had no effect on MAP or HR and the results obtained are therefore not represented in the figure. In brief, co-administration of COMPOUND and amlodipine decreased MAP beyond the predicted (calculated) values, demonstrating synergism between the two molecules. In contrast to MAP, HR was not affected in any of the treatment groups.

Example H: Chronic Effects of COMPOUND in Deoxycorticosterone Acetate Salt Rats The chronic effects of repeated administrations of doses of 1, 10 and 100 mg/kg/day of COMPOUND, in particular mean arterial blood pressure (hereafter "MAP"), and heart rate (hereafter "HR"), were evaluated in conscious, male hypertensive deoxycorticosterone acetate salt rats (hereafter "DOCA-salt rats"—see details about this model in Gavras et al., *Circ. Res.* (1975), 36, 300-309). In the DOCA-salt rats, hypertension is induced by the combination of unilateral nephrectomy, implantation of pellets of the mineralocorticoid analog DOCA, and provision of 1% sodium chloride in drinking water. The results of the DOCA-salt rats treated with COMPOUND were compared to those obtained for Wistar rats or for DOCA-salt rats that received only the vehicle (4% gelatin aquous solution).

a) The results obtained regarding MAP are summarised in FIG. 16 wherein each data point is presented as a 24-hour mean. 6 rats were used for each of the 5 test groups (Wistar control rats [bottom line], DOCA-salt control rats [$2^{nd}$ line from top at day 28] and DOCA-salt rats receiving repeated administrations of doses of 1 mg/kg/day [top line at day 28], 10 mg/kg/day [$3^{rd}$ line from top at day 28] and 100 mg/kg/day [$4^{th}$ line from top at day 28] of COMPOUND). In brief, oral administration of COMPOUND for 4 weeks dose-dependently attenuated the DOCA-salt-induced increase in MAP without changing HR.

b) The results obtained regarding renal vascular resistance are summarised in FIG. 17 wherein:
DOCA æ 2w represents DOCA-salt rats sacrified just before initiation of treatment with COMPOUND; and
the "*" symbol in represents a statistical significance factor $p<0.05$ when using a one way ANOVA followed by a Newmal-Keuls multiple comparisons post-hoc test.

In summary, based on these tests, chronic oral administration of COMPOUND to DOCA-salt rats dose-dependently increased renal blood flow and decreased renal vascular resistance. COMPOUND also tended to decrease left ventricular hypertrophy, as suggested by the dose-dependent decrease in plasma concentrations of N-terminal pro-brain natriuretic peptide (NTproBNP).

Example I: Effects of COMPOUND, Alone or in Combination with an ACE Inhibitor or an ARB, in Animal Models of Diabetes The effects of COMPOUND can be assessed in diabetic rodent models (in this regard, see the models described in the following references: Sen et al, *Life Sci.* (2012), 91(13-14), 658-668; Janiak et al., *Eur. J. Pharmacol.* (2006), 534, 271-279; and Iglarz et al, *J. Pharmacol. Exp. Ther.* (2008), 327(3), 736-745). In particular, the effect of COMPOUND, alone or in combination, on glucose tolerance, insulinemia and end organ damage can be investigated. End organ damage includes: vascular function, renal function (e.g. proteinuria), cardiac function and remodelling and any other target organ affected by diabetes (e.g. the eye).

Example J: Evaluation of the Effect of COMPOUND on Fluid Retention

A decrease in haematocrit (Hct) or haemoglobin occurs secondary to an increase in plasma volume and can be used as a marker of fluid retention. A single oral dose of aprocitentan (1-30 mg/kg) or vehicle (gelatin) was administered by gavage to male Wistar rats. Twenty-four hours after administration, sublingual blood was sampled under isoflurane-induced anesthesia. Haematocrit was measured using a hematology analyser. COMPOUND did not impact on haematocrit (Hct) suggesting low liability on fluid retention (FIG. 18).

Comparison Example 1: Acute Effects of Spironolactone Used in Combination with Valsartan in Spontaneaously Hypertensive Rats The acute effects of spironolactone on blood pressure, in particular on mean arterial blood pressure (hereafter "MAP"), and heart rate (hereafter "HR") in combination with valsartan, each administered orally as single doses, were also evaluated by means of telemetry in conscious, male spontaneaously hypertensive rats (hereafter "SHRs"—see details about this model in Atanur et al., *Genome Res.* (2010), 20, 791-803) using a protocol analog to that described in Example D.

Unlike for COMPOUND, no synergistic effect was seen on MAP reduction for the combination of spironolactone treatment with valsartan treatment.

Comparison Example 2: Acute Effects of Spironolactone Used in Combination with Valsartan in Deoxycorticosterone Acetate Salt Rats The acute effects of spironolactone on blood pressure, in particular on mean arterial blood pressure (hereafter "MAP"), and heart rate (hereafter "HR") in combination with valsartan, each administered orally as single doses, were also evaluated by means of telemetry in conscious, male hypertensive deoxycorticosterone acetate salt rats (hereafter "DOCA-salt rats"—see details about this model in Gavras et al., *Circ. Res.* (1975), 36, 300-309) using a protocol analog to that described in Example E.

Unlike for COMPOUND, no synergistic effect was seen on MAP reduction for the combination of spironolactone treatment with valsartan treatment.

Comparison Example 3: Acute Effects of Spironolactone Used in Combination with Enalapril in Spontaneaously Hypertensive Rats The acute effects of spironolactone on blood pressure, in particular on mean arterial blood pressure (hereafter "MAP"), and heart rate (hereafter "HR") in combination with valsartan, each administered orally as single doses, were also evaluated by means of telemetry in conscious, male spontaneaously hypertensive rats (hereafter "SHRs"—see details about this model in Atanur et al., *Genome Res.* (2010), 20, 791-803) using a protocol analog to that described in Example F.

Unlike for COMPOUND, no synergistic effect was seen on MAP reduction for the combination of spironolactone treatment with enalapril treatment.

The invention claimed is:

1. A pharmaceutical unit dosage form for oral administration, wherein the pharmaceutical unit dosage form comprises a crystalline form of {5-(4-bromo-phenyl)-6-[2-(5-bromo-pyrimidin-2-yloxy)-ethoxy]-pyrimidin-4-yl}-sulfamide:

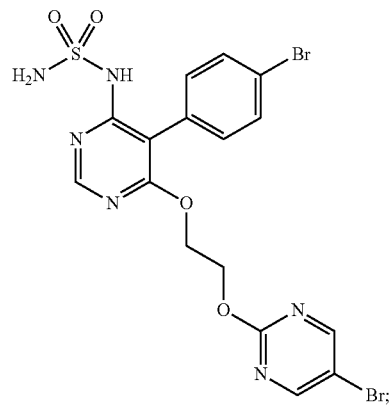

characterized by:
the presence of peaks in the X-ray powder diffraction diagram at the following angles of refraction 2θ: 17.8°, 20.0°, and 23.5°; or
the presence of peaks in the X-ray powder diffraction diagram at the following angles of refraction 2θ: 9.7°, 15.7°, and 22.0°;
wherein said X-ray powder diffraction diagram is obtained by using combined Cu Kα1 and Kα2 radiation, without Kα2 stripping, and the accuracy of the 2θ values is in the range of 2θ+/−0.2°, and wherein said pharmaceutical unit dosage form is suitable for oral administration of 10 to 50 mg per day of {5-(4-bromo-phenyl)-6-[2-(5-bromo-pyrimidin-2-yloxy)-ethoxy]-pyrimidin-4-yl}-sulfamide.

2. The pharmaceutical unit dosage form according to claim 1, wherein said pharmaceutical unit dosage form is a solid and comprises:
said crystalline form of {5-(4-bromo-phenyl)-6-[2-(5-bromo-pyrimidin-2-yloxy)-ethoxy]-pyrimidin-4-yl}-sulfamide in a total amount from 5 to 25% in weight based on the total weight of the pharmaceutical unit dosage form;
microcrystalline cellulose in a total amount from 20 to 30% in weight based on the total weight of the pharmaceutical unit dosage form;
lactose in a total amount from 40 to 65% in weight based on the total weight of the pharmaceutical unit dosage form;
hydroxypropylcellulose in a total amount from 1 to 3% in weight based on the total weight of the pharmaceutical unit dosage form;
croscarmellose sodium in a total amount from 2 to 8% in weight based on the total weight of the pharmaceutical unit dosage form; and
magnesium stearate in a total amount from 0.2 to 2% in weight based on the total weight of the pharmaceutical unit dosage form.

3. The pharmaceutical unit dosage form according to claim 1, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 17.8°, 20.0°, and 23.5°; wherein said X-ray powder diffraction diagram is obtained by using combined Cu Kα1 and Kα2 radiation, without Kα2 stripping, and the accuracy of the 2θ values is in the range of 2θ+/−0.2°.

4. The pharmaceutical unit dosage form according to claim 2, wherein said crystalline form of {5-(4-bromophenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 17.8°, 20.0°, and 23.5°; wherein said X-ray powder diffraction diagram is obtained by using combined Cu Kα1 and Kα2 radiation, without Kα2 stripping, and the accuracy of the 2θ values is in the range of 2θ+/−0.2°.

5. The pharmaceutical unit dosage form according to claim 1, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping, and the accuracy of the 2θ values is in the range of 2θ+/−0.2°.

6. The pharmaceutical unit dosage form according to claim 1, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 7.8°, 9.7°, 15.7°, 19.8° and 22.0°; wherein said X-ray powder diffraction diagram is obtained by using combined Cu Kα1 and Kα2 radiation, without Kα2 stripping, and the accuracy of the 2θ values is in the range of 2θ+/−0.2°.

7. The pharmaceutical unit dosage form according to claim 1, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping, and the accuracy of the 2θ values is in the range of 2θ+/−0.2°.

8. The pharmaceutical unit dosage form according to claim 2, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping, and the accuracy of the 2θ values is in the range of 2θ+/−0.2°.

9. The pharmaceutical unit dosage form according to claim 2, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 7.8°, 9.7°, 15.7°, 19.8° and 22.0°; wherein said X-ray powder diffraction diagram is obtained by using combined Cu Kα1 and Kα2 radiation, without Kα2 stripping, and the accuracy of the 2θ values is in the range of 2θ+/−0.2°.

10. The pharmaceutical unit dosage form according to claim 2, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 9.8°, 9.9°, 11.7°, 17.8°, 18.6°, 20.0°, 21.5°, 22.8°, 23.2° and 23.5°; wherein said X-ray powder diffraction diagram is obtained by using combined Cu Kα1 and Kα2 radiation, without Kα2 stripping, and the accuracy of the 2θ values is in the range of 2θ+/−0.2°.

11. The pharmaceutical unit dosage form according to claim 5, wherein said crystalline form of {5-(4-bromo-phenyl)-6-[2-(5-bromo-pyrimidin-2-yloxy)-ethoxy]-pyrimidin-4-yl}-sulfamide essentially shows the X-ray powder diffraction pattern as depicted in FIG. 1.

12. The pharmaceutical unit dosage form according to claim 8, wherein said crystalline form of {5-(4-bromo-phenyl)-6-[2-(5-bromo-pyrimidin-2-yloxy)-ethoxy]-pyrimidin-4-yl}-sulfamide essentially shows the X-ray powder diffraction pattern as depicted in FIG. 1.

13. The pharmaceutical unit dosage form according to claim 1, wherein said pharmaceutical unit dosage form is a tablet.

14. The pharmaceutical unit dosage form according to claim 2, wherein said pharmaceutical unit dosage form is a tablet.

15. The pharmaceutical unit dosage form according to claim 5, wherein said pharmaceutical unit dosage form is a tablet.

16. The pharmaceutical unit dosage form according to claim 8, wherein said pharmaceutical unit dosage form is a tablet.

17. A tablet, wherein said tablet comprises a crystalline form of {5-(4-bromo-phenyl)-6-[2-(5-bromo-pyrimidin-2-yloxy)-ethoxy]-pyrimidin-4-yl}-sulfamide:

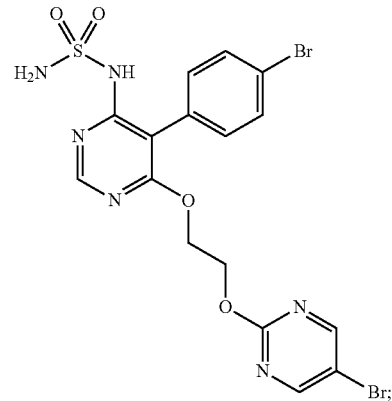 [SMILES: NS(=O)(=O)Nc1ncnc(OCCOc2ncc(Br)cn2)c1-c1ccc(Br)cc1]

characterized by:
the presence of peaks in the X-ray powder diffraction diagram at the following angles of refraction 2θ: 17.8°, 20.0°, and 23.5°; or
the presence of peaks in the X-ray powder diffraction diagram at the following angles of refraction 2θ: 9.7°, 15.7°, and 22.0°;
wherein said X-ray powder diffraction diagram is obtained by using combined Cu Kα1 and Kα2 radiation, without Kα2 stripping, and the accuracy of the 2θ values is in the range of 2θ+/−0.2°, and wherein said tablet comprises 25 mg of {5-(4-bromo-phenyl)-6-[2-(5-bromo-pyrimidin-2-yloxy)-ethoxy]-pyrimidin-4-yl}-sulfamide.

18. The tablet according to claim 17, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping, and the accuracy of the 2θ values is in the range of 2θ+/−0.2°.

19. A tablet, wherein said tablet comprises a crystalline form of {5-(4-bromo-phenyl)-6-[2-(5-bromo-pyrimidin-2-yloxy)-ethoxy]-pyrimidin-4-yl}-sulfamide:

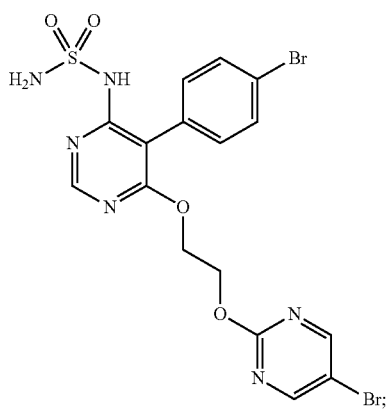 [SMILES: NS(=O)(=O)Nc1ncnc(OCCOc2ncc(Br)cn2)c1-c1ccc(Br)cc1]

characterized by:
the presence of peaks in the X-ray powder diffraction diagram at the following angles of refraction 2θ: 17.8°, 20.0°, and 23.5°; or
the presence of peaks in the X-ray powder diffraction diagram at the following angles of refraction 2θ: 9.7°, 15.7°, and 22.0°;
wherein said X-ray powder diffraction diagram is obtained by using combined Cu Kα1 and Kα2 radiation, without Kα2 stripping, and the accuracy of the 2θ values is in the range of 2θ+/−0.2°, and wherein said tablet comprises 12.5 mg of {5-(4-bromo-phenyl)-6-[2-(5-bromo-pyrimidin-2-yloxy)-ethoxy]-pyrimidin-4-yl}-sulfamide.

20. The tablet according to claim 19, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping, and the accuracy of the 2θ values is in the range of 2θ+/−0.2°.

21. A process for preparing a pharmaceutical composition comprising {5-(4-bromo-phenyl)-6-[2-(5-bromo-pyrimidin-2-yloxy)-ethoxy]-pyrimidin-4-yl}-sulfamide:

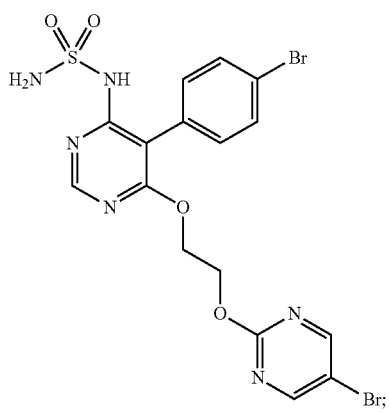 [SMILES: NS(=O)(=O)Nc1ncnc(OCCOc2ncc(Br)cn2)c1-c1ccc(Br)cc1]

wherein said process comprises mixing a crystalline form of {5-(4-bromo-phenyl)-6-[2-(5-bromo-pyrimidin-2-yloxy)-ethoxy]-pyrimidin-4-yl}-sulfamide characterized by:
the presence of peaks in the X-ray powder diffraction diagram at the following angles of refraction 2θ: 17.8°, 20.0°, and 23.5°; or
the presence of peaks in the X-ray powder diffraction diagram at the following angles of refraction 2θ: 9.7°, 15.7°, and 22.0°;
wherein said X-ray powder diffraction diagram is obtained by using combined Cu Kα1 and Kα2 radiation, without Kα2 stripping, and the accuracy of the 2θ values is in the range of 2θ+/−0.2°, and at least one therapeutically inert excipient.

22. The process according to claim 21, wherein said pharmaceutical composition is a pharmaceutical unit dosage form suitable for oral administration of 10 to 50 mg per day of {5-(4-bromo-phenyl)-6-[2-(5-bromo-pyrimidin-2-yloxy)-ethoxy]-pyrimidin-4-yl}-sulfamide.

23. The process according to claim 21, wherein said process comprises mixing the crystalline form of {5-(4-bromo-phenyl)-6-[2-(5-bromo-pyrimidin-2-yloxy)-ethoxy]-pyrimidin-4-yl}-sulfamide with microcrystalline cellulose, lactose, hydroxypropylcellulose, croscarmellose sodium and magnesium stearate.

24. The process according to claim 21, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping, and the accuracy of the 2θ values is in the range of 2θ+/−0.2°.

25. The process according to claim 23, wherein said crystalline form of {5-(4-bromo-phenyl)-6-[2-(5-bromo-pyrimidin-2-yloxy)-ethoxy]-pyrimidin-4-yl}-sulfamide is characterized by the presence of peaks in the X-ray powder diffraction diagram at the following angles of refraction 2θ: 17.8°, 18.6°, 20.0°, 23.2° and 23.5°; wherein said X-ray powder diffraction diagram is obtained by using combined Cu Kα1 and Kα2 radiation, without Kα2 stripping, and the accuracy of the 2θ values is in the range of 2θ+/−0.2°.

\* \* \* \* \*